United States Patent
Nakamura et al.

(10) Patent No.: US 11,160,902 B2
(45) Date of Patent: Nov. 2, 2021

(54) CARTILAGE REGENERATIVE MATERIAL AND METHOD FOR PRODUCING SAME

(71) Applicants: FUJIFILM Corporation, Tokyo (JP); JAPAN TISSUE ENGINEERING CO., LTD., Gamagori (JP)

(72) Inventors: Kentaro Nakamura, Ashigarakami-gun (JP); Hayato Miyoshi, Ashigarakami-gun (JP); Satoko Hada, Gamagori (JP); Masatoki Watanabe, Gamagori (JP)

(73) Assignees: FUJIFILM Corporation, Tokyo (JP); JAPAN TISSUE ENGINEERING CO., LTD., Gamagori (JP)

( * ) Notice: Subject to any disclaimer, the term of this patent is extended or adjusted under 35 U.S.C. 154(b) by 122 days.

(21) Appl. No.: 15/705,669

(22) Filed: Sep. 15, 2017

(65) Prior Publication Data
US 2019/0216976 A1    Jul. 18, 2019

Related U.S. Application Data

(63) Continuation of application No. PCT/JP2016/058541, filed on Mar. 17, 2016.

(30) Foreign Application Priority Data

Mar. 18, 2015    (JP) .............................. JP2015-054887

(51) Int. Cl.
| | |
|---|---|
| *A61L 27/56* | (2006.01) |
| *A61L 27/22* | (2006.01) |
| *A61L 27/36* | (2006.01) |
| *A61L 27/38* | (2006.01) |
| *A61L 27/58* | (2006.01) |
| *A61L 27/00* | (2006.01) |
| *A61L 27/54* | (2006.01) |
| *A61L 27/24* | (2006.01) |

(52) U.S. Cl.
CPC ............. *A61L 27/222* (2013.01); *A61L 27/00* (2013.01); *A61L 27/225* (2013.01); *A61L 27/227* (2013.01); *A61L 27/24* (2013.01); *A61L 27/3612* (2013.01); *A61L 27/3633* (2013.01); *A61L 27/3654* (2013.01); *A61L 27/3817* (2013.01); *A61L 27/3852* (2013.01); *A61L 27/54* (2013.01); *A61L 27/56* (2013.01); *A61L 27/58* (2013.01); *A61L 2430/06* (2013.01); *A61L 2430/24* (2013.01)

(58) Field of Classification Search
None
See application file for complete search history.

(56) References Cited

U.S. PATENT DOCUMENTS

| | | | | |
|---|---|---|---|---|
| 5,041,138 A | * | 8/1991 | Vacanti | A61F 2/02 424/422 |
| 5,447,966 A | * | 9/1995 | Hermes | A01N 37/36 424/423 |
| 6,387,693 B2 | * | 5/2002 | Rieser | A61F 2/30756 435/1.1 |
| 2002/0177903 A1 | | 11/2002 | Geistlich et al. | |
| 2003/0050709 A1 | | 3/2003 | Noth et al. | |
| 2004/0062809 A1 | | 4/2004 | Honiger et al. | |
| 2004/0234577 A1 | | 11/2004 | Geistlich et al. | |
| 2006/0212125 A1 | | 9/2006 | Okihana | |
| 2007/0160681 A1 | | 7/2007 | Park et al. | |
| 2009/0228105 A1 | * | 9/2009 | Son | A61K 35/28 623/14.12 |
| 2011/0184381 A1 | | 7/2011 | Shintani | |
| 2012/0148639 A1 | | 6/2012 | Tamada et al. | |
| 2012/0165263 A1 | | 6/2012 | Hiratsuka et al. | |
| 2012/0329157 A1 | | 12/2012 | Nakamura | |
| 2013/0004549 A1 | | 1/2013 | Nakamura et al. | |
| 2013/0071441 A1 | | 3/2013 | Iwazawa et al. | |
| 2014/0378662 A1 | | 12/2014 | Oya et al. | |
| 2015/0352252 A1 | | 12/2015 | Nakamura et al. | |

FOREIGN PATENT DOCUMENTS

| | | |
|---|---|---|
| AU | 200014990 A1 | 8/2000 |
| CN | 1280509 A | 1/2001 |
| CN | 1933859 A | 3/2007 |
| CN | 102625717 A | 8/2012 |

(Continued)

OTHER PUBLICATIONS

Pulkkinen et al., The use of recombinant human type II collagen for articular cartilage tissue engineering, Dissertation in Health Sciences, No. 142, 2012 (Year: 2012).*

Pettersson et al., Biodegradable gelatin microcarriers in tissue engineering, In vitro studies on cartilage and bone, Dissertation No. 1147, 2009 (Year: 2009).*

Japanese Office Action and English translation for Application No. 2017-506614, dated May 22, 2018.

Huang et al., "Solid freeform-fabricated scaffolds designed to carry multicellular mesenchymal stem cell spheroids for cartilage regeneration," European Cells and Materials, vol. 26, 2013, pp. 179-194.

(Continued)

*Primary Examiner* — Scott Long
*Assistant Examiner* — Evelyn Y Pyla
(74) *Attorney, Agent, or Firm* — Birch, Stewart, Kolasch & Birch, LLP

(57) ABSTRACT

An object of the invention is to provide a cartilage regenerative material that suppresses infiltration of fibrous soft tissue and brings about satisfactory cartilage regeneration, and a method for producing the cartilage regenerative material. Provided is a cartilage regenerative material including a porous body of a biocompatible polymer and a biocompatible polymer film, in which the porous body contains chondrocytes and cartilage matrix, and the cartilage matrix exists in a region of 10% or more of a region extending from the surface of the transplant face of the porous body to a depth of 150 μm along the thickness.

17 Claims, 17 Drawing Sheets

Specification includes a Sequence Listing.

(56) References Cited

FOREIGN PATENT DOCUMENTS

| | | | |
|---|---|---|---|
| CN | 102791301 A | 11/2012 | |
| CN | 102858381 A | 1/2013 | |
| CN | 104244999 A | 12/2014 | |
| EP | 2543397 A1 | 1/2013 | |
| JP | 2001-293081 A | 10/2001 | |
| JP | 2001-519210 A | 10/2001 | |
| JP | 2003-275294 A | 9/2003 | |
| JP | 2004-501700 A | 1/2004 | |
| JP | 2004-357694 A | 12/2004 | |
| JP | 2005-152006 A | 6/2005 | |
| JP | 2006-289062 A | 10/2006 | |
| JP | 4122280 B2 | 7/2008 | |
| JP | 2010-535602 A | 11/2010 | |
| JP | 2014-12114 A | 1/2014 | |
| JP | 2015054887 * | 3/2015 | ............. A61L 27/00 |
| WO | WO 2006/022671 A1 | 3/2006 | |
| WO | WO 2011/021712 A1 | 2/2011 | |
| WO | WO 2011/108517 A1 | 9/2011 | |
| WO | WO 2011/108537 A1 | 9/2011 | |
| WO | WO 2014/133081 A1 | 9/2014 | |

OTHER PUBLICATIONS

International Preliminary Report on Patentability and Written Opinion of the International Searching Authority (Forms PCT/IB/373, PCT/IB/326 and PCT/ISA/237), dated Sep. 28, 2017, for International Application No. PCT/JP2016/058540, with an English translation of the Written Opinion.

International Preliminary Report on Patentability and Written Opinion of the International Searching Authority (Forms PCT/IB/373, PCT/IB/326 and PCT/ISA/237), dated Sep. 28, 2017, for International Application No. PCT/JP2016/058541, with an English translation of the Written Opinion.

International Search Report and English translation (Form PCT/ISA/210), dated Jun. 21, 2016, for International Application No. PCT/JP2016/058541.

International Search Report and English translation (Form PCT/ISA/210), dated Jun. 7, 2016, for International Application No. PCT/JP2016/058540.

Lee et al., "Transplantation of scaffold-free spheroids composed of synovium-derived cells and chondrocytes for the treatment of cartilage defects of the knee," European Cells and Materials, vol. 22, 2011, pp. 275-290.

Toh et al., "Advances in mesenchymal stem cell-based strategies for cartilage repair and regeneration," Stem Cell Reviews and Reports, vol. 10, 2014 (published online May 29, 2014), pp. 686-696.

Yoshioka, "Recombinant collagen technology applying on regenerative medicine," Medical Science Digest, vol. 40, No. 12, 2014, pp. 46-49 (6 pages total).

European Office Action for European Application No. 16765074.6, dated May 7, 2019.

U.S. Non-Final Office Action dated Jul. 22, 2019, for U.S. Appl. No. 15/705,826.

Japanese Office Action, dated Oct. 16, 2018, for corresponding Japanese Application No. 2017-506615, with an English machine translation.

Extended European Search Report for corresponding European Application No. 16765074.6, dated Feb. 14, 2018.

Extended European Search Report for corresponding European Application No. 16765075.3, dated Feb. 15, 2018.

Japanese Notification of Reasons for Refusal for Japanese Application No. 2017-506615, dated Apr. 24, 2018, with machine translation.

Ponticello et al., "Gelatin-Based Resorbable Spong as a Carrier Matrix for Human Mesenchymal Stem Cells in Cartilage Regeneration Therapy," J Biomed Mater Res, vol. 52, 2000, pp. 246-255.

Raghunath et al., "Advancing Cartilage Tissue Engineering: the Application of Stem Cell Technology," Current Opinions in Biotechnology, vol. 16, 2005 (published on web Sep. 8, 2005), pp. 503-509.

Chinese Office Action and Search Report, dated Nov. 13, 2019 for corresponding Chinese Application No. 201680016571.1, with an English translation of the Chinese Office Action.

Chinese Office Action and Search Report for Chinese Application No. 201680016000.8, dated Jan. 6, 2020, with English translation.

Chinese Office Action for corresponding Chinese Application No. 201680016571.1, dated Jul. 30, 2020, with an English translation.

European Communication pursuant to Article 94(3) EPC for corresponding European Application No. 16765075.3, dated Oct. 26, 2020.

U.S. Final Office Action for U.S. Appl. No. 16/660,003, dated May 5, 2021.

Chinese Office Action for Chinese Application No. 201680016000.8, dated Sep. 22, 2020, with English translation.

European Office Action for European Application No. 16765074.6, dated Aug. 27, 2020.

U.S. Office Action for U.S. Appl. No. 16/660,003, dated Oct. 15, 2020.

Zhang et al., "The Role of Tissue Engineering Articular Cartilage Repair and Regeneration," Crit. Rev. Biomed. Eng., vol. 37, No. 1-2, 2009, pp. 1-44.

Chinese Office Action for Application No. 201680016000.8, dated Feb. 22, 2021, with machine English translation.

Chinese Office Action for Application No. 201680016571.1, dated Feb. 22, 2021, with machine English translation.

Chinese Office Action and Search Report for Chinese Application No. 201680016571.1, dated Jul. 21, 2021, with English translation of the Office Action.

Chinese Office Action for Chinese Application No. 201680016000.8, dated May 27, 2021, with English translation.

* cited by examiner

SUPPRESSION OF
FIBROUS SOFT TISSUE D

CARTILAGE
REGENERATION C

SUPPRESSION OF
FIBROUS SOFT TISSUE B

CARTILAGE
REGENERATION C

FILM WITH DEGREE OF CROSSLINKING OF 13

RESULTS IN SIX MONTHS
AFTER TRANSPLANTATION
SUPPRESSION OF FIBROUS
SOFT TISSUE A
CARTILAGE REGENERATION A

FILM WITH DEGREE OF CROSSLINKING OF 6

RESULTS IN SIX MONTHS
AFTER TRANSPLANTATION
SUPPRESSION OF FIBROUS
SOFT TISSUE A
CARTILAGE REGENERATION AA

SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

```
Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
```

```
                355                 360                 365
Pro Gly Lys Asp Gly Val Arg Gly Leu Ala Gly Pro Pro Gly Ala Pro
            370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 4
```

```
Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
```

```
<220> FEATURE:
<223> OTHER INFORMATION: Description of Artificial Sequence: adhesive
      sequence

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
```

```
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
```

```
<222> LOCATION: (110)..(110)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
```

```
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
```

-continued

```
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (287)..(287)
```

```
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (302)..(302)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (326)..(326)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (341)..(341)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
```

```
<222> LOCATION: (347)..(347)
<223> OTHER INFORMATION: Xaa can be any naturally occurring amino acid
<220> FEATURE:
<221> NAME/KEY: misc_feature
<222> LOCATION: (350)..(350)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (386)..(386)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
```

```
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (413)..(413)
<223> OTHER INFORMATION: Xaa can be any naturally occurring amino acid
<220> FEATURE:
<221> NAME/KEY: misc_feature
<222> LOCATION: (416)..(416)
<223> OTHER INFORMATION: Xaa can be any naturally occurring amino acid
<220> FEATURE:
<221> NAME/KEY: misc_feature
<222> LOCATION: (419)..(419)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (425)..(425)
<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (437)..(437)
<223> OTHER INFORMATION: Xaa can be any naturally occurring amino acid
<220> FEATURE:
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (446)..(446)
<223> OTHER INFORMATION: Xaa can be any naturally occurring amino acid
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: misc_feature
<222> LOCATION: (452)..(452)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: misc_feature
<222> LOCATION: (458)..(458)
<223> OTHER INFORMATION: Xaa can be any naturally occurring amino acid
<220> FEATURE:
<221> NAME/KEY: misc_feature
<222> LOCATION: (461)..(461)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
```

-continued

```
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (470)..(470)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (485)..(485)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (491)..(491)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (509)..(509)
<223> OTHER INFORMATION: Xaa can be any naturally occurring amino acid
<220> FEATURE:
<221> NAME/KEY: misc_feature
<222> LOCATION: (512)..(512)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (521)..(521)
<223> OTHER INFORMATION: Xaa can be any naturally occurring amino acid
<220> FEATURE:
<221> NAME/KEY: misc_feature
<222> LOCATION: (524)..(524)
```

```
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (533)..(533)
<223> OTHER INFORMATION: Xaa can be any naturally occurring amino acid
<220> FEATURE:
<221> NAME/KEY: misc_feature
<222> LOCATION: (536)..(536)
<223> OTHER INFORMATION: Xaa can be any naturally occurring amino acid
<220> FEATURE:
<221> NAME/KEY: misc_feature
<222> LOCATION: (539)..(539)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (554)..(554)
<223> OTHER INFORMATION: Xaa can be any naturally occurring amino acid
<220> FEATURE:
<221> NAME/KEY: misc_feature
<222> LOCATION: (557)..(557)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (566)..(566)
<223> OTHER INFORMATION: Xaa can be any naturally occurring amino acid
<220> FEATURE:
<221> NAME/KEY: misc_feature
<222> LOCATION: (569)..(569)
<223> OTHER INFORMATION: Xaa can be any naturally occurring amino acid

<400> SEQUENCE: 11

Gly Ala Pro Gly Xaa Tyr Gly Xaa Tyr Gly Xaa Tyr Gly Xaa Tyr Gly
1               5                   10                  15

Xaa Tyr Gly Xaa Tyr Gly Xaa Tyr Gly Xaa Tyr Gly Xaa Tyr Gly Xaa
            20                  25                  30

Tyr Gly Xaa Tyr Gly Xaa Tyr Gly Xaa Tyr Gly Xaa Tyr Gly Xaa Tyr
        35                  40                  45

Gly Xaa Tyr Gly Xaa Tyr Gly Xaa Tyr Gly Xaa Tyr Gly Xaa Tyr Gly
    50                  55                  60

Xaa Tyr Gly Xaa Tyr Gly Xaa Tyr Gly Xaa Tyr Gly Xaa Tyr Gly Xaa
65                  70                  75                  80
```

```
Tyr Gly Xaa Tyr Gly Xaa Tyr Gly Xaa Tyr Gly Xaa Tyr
             85                  90                  95

Gly Xaa Tyr Gly Xaa Tyr Gly Xaa Tyr Gly Xaa Tyr Gly
            100                 105                 110

Xaa Tyr Gly Xaa Tyr Gly Xaa Tyr Gly Xaa Tyr Gly Xaa
            115                 120                 125

Tyr Gly Xaa Tyr Gly Xaa Tyr Gly Xaa Tyr Gly Xaa Tyr
            130                 135                 140

Gly Xaa Tyr Gly Xaa Tyr Gly Xaa Tyr Gly Xaa Tyr Gly
145                 150                 155                 160

Xaa Tyr Gly Xaa Tyr Gly Xaa Tyr Gly Xaa Tyr Gly Xaa
            165                 170                 175

Tyr Gly Xaa Tyr Gly Xaa Tyr Gly Xaa Tyr Gly Xaa Tyr
            180                 185                 190

Gly Xaa Tyr Gly Xaa Tyr Gly Xaa Tyr Gly Xaa Tyr Gly
            195                 200                 205

Xaa Tyr Gly Xaa Tyr Gly Xaa Tyr Gly Xaa Tyr Gly Xaa
            210                 215                 220

Tyr Gly Xaa Tyr Gly Xaa Tyr Gly Xaa Tyr Gly Xaa Tyr
225                 230                 235                 240

Gly Xaa Tyr Gly Xaa Tyr Gly Xaa Tyr Gly Xaa Tyr Gly
            245                 250                 255

Xaa Tyr Gly Xaa Tyr Gly Xaa Tyr Gly Xaa Tyr Gly Xaa
            260                 265                 270

Tyr Gly Xaa Tyr Gly Xaa Tyr Gly Xaa Tyr Gly Xaa Tyr
            275                 280                 285

Gly Xaa Tyr Gly Xaa Tyr Gly Xaa Tyr Gly Xaa Tyr Gly
            290                 295                 300

Xaa Tyr Gly Xaa Tyr Gly Xaa Tyr Gly Xaa Tyr Gly Xaa
305                 310                 315                 320

Tyr Gly Xaa Tyr Gly Xaa Tyr Gly Xaa Tyr Gly Xaa Tyr
            325                 330                 335

Gly Xaa Tyr Gly Xaa Tyr Gly Xaa Tyr Gly Xaa Tyr Gly
            340                 345                 350

Xaa Tyr Gly Xaa Tyr Gly Xaa Tyr Gly Xaa Tyr Gly Xaa
            355                 360                 365

Tyr Gly Xaa Tyr Gly Xaa Tyr Gly Xaa Tyr Gly Xaa Tyr
            370                 375                 380

Gly Xaa Tyr Gly Xaa Tyr Gly Xaa Tyr Gly Xaa Tyr Gly
385                 390                 395                 400

Xaa Tyr Gly Xaa Tyr Gly Xaa Tyr Gly Xaa Tyr Gly Xaa
            405                 410                 415

Tyr Gly Xaa Tyr Gly Xaa Tyr Gly Xaa Tyr Gly Xaa Tyr
            420                 425                 430

Gly Xaa Tyr Gly Xaa Tyr Gly Xaa Tyr Gly Xaa Tyr Gly
            435                 440                 445

Xaa Tyr Gly Xaa Tyr Gly Xaa Tyr Gly Xaa Tyr Gly Xaa
            450                 455                 460

Tyr Gly Xaa Tyr Gly Xaa Tyr Gly Xaa Tyr Gly Xaa Tyr
465                 470                 475                 480

Gly Xaa Tyr Gly Xaa Tyr Gly Xaa Tyr Gly Xaa Tyr Gly
            485                 490                 495

Xaa Tyr Gly Xaa Tyr Gly Xaa Tyr Gly Xaa Tyr Gly Xaa
```

-continued

```
                500                 505                 510
Tyr Gly Xaa Tyr Gly Xaa Tyr Gly Xaa Tyr Gly Xaa Tyr Gly Xaa Tyr
            515                 520                 525

Gly Xaa Tyr Gly Xaa Tyr Gly Xaa Tyr Gly Xaa Tyr Gly Xaa Tyr Gly
        530                 535                 540

Xaa Tyr Gly Xaa Tyr Gly Xaa Tyr Gly Xaa Tyr Gly Xaa Tyr Gly Xaa
545                 550                 555                 560

Tyr Gly Xaa Tyr Gly Xaa Tyr Gly Xaa Tyr Gly
            565                 570
```

CARTILAGE REGENERATIVE MATERIAL AND METHOD FOR PRODUCING SAME

CROSS-REFERENCE TO RELATED APPLICATIONS

This application is a Continuation of PCT International Application No. PCT/JP2016/058541 filed on Mar. 17, 2016, which claims priority under 35 U.S.C § 119(a) to Japanese Patent Application No. 2015-054887 filed on Mar. 18, 2015. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2019-03-19 2870-0680PUS1 ST25-txt" created on Mar. 19, 2019 and is 31,880 bytes in size. The sequence listing contained in this .txt file is part of the specification and is hereby incorporated by reference herein in its entirety.

BACKGROUND OF THE INVENTION

1. Field of the Invention

The present invention relates to a cartilage regenerative material including a porous body of a biocompatible polymer and a biocompatible polymer film, and a method for producing the cartilage regenerative material.

2. Description of the Related Art

Generally, articular osteochondral defects are not likely to be accompanied by spontaneous regeneration, and thus, regenerative medicine based on cell transplantation therapy has been actively attempted. Specifically, transplanting cells in the form of a cell construct as cultured cartilage by utilizing a scaffold has been attempted.

WO2011/108537A describes a cell support formed from a porous body constructed from a biodegradable material and having predetermined characteristics. The cell support described in WO2011/108537A can be used as a carrier for culturing cells, and in the Examples, it is described that a porous body formed from a recombinant gelatin or a naturally occurring gelatin material is used as a cell support.

JP2001-519210A describes a multilayer film composed of a matrix layer formed mainly from type II collagen and having a sponge-like open structure; and at least one barrier layer having a relatively impermeable closed structure. It is described in JP2001-519210A that the multilayer film is appropriate for the use intended particularly for in vivo regeneration of a bone tissue or a cartilage tissue.

SUMMARY OF THE INVENTION

In regard to articular osteochondral defects, a transplantation therapy of injecting a suspension of cells is known; however, simple administration of cells does not lead to engraftment of the cells onto the site of defect, and a sufficient regeneration effect is not obtained. Furthermore, it has been attempted in many cases to transplant cells in the form of a cell construct as cultured cartilage by utilizing a scaffold as described above; however, in reality, there are occasions in which, upon transplantation of cultured cartilage, the cultured cartilage becomes bone or fibrous soft tissue due to infiltration of inflammation or infiltration of blood vessels. Thus, the effect of cartilage regeneration is not necessarily sufficient, and thus there is a demand for a cell construct exhibiting a superior cartilage regeneration effect.

The cell support described in WO2011/108537A is formed from a porous body that is constructed from a biodegradable material and has a predetermined void volume, a predetermined average pore size, hole interconnecting pores, and a predetermined water absorption rate. The cell support is useful as a bone regenerative material; however, it is unclear about cartilage regenerative capacity.

It is presumed from JP2001-519210A that type II collagen may be useful for the culture of chondrocytes; however, transplantation of type II collagen into a joint may induce arthritis (collagen-induced arthritis), and may cause injury in peripheral normal articular cartilage. Therefore, it is not preferable to use type II collagen in reality. Even in a case in which the barrier layer described in JP2001-519210A is provided, in fact, ossification of cartilage or infiltration of fibrous soft tissue caused by infiltration of inflammation or infiltration of blood vessels cannot be suppressed.

As described above, it has been a problem that in transplantation of cultured cartilage, a cultured cartilage part that has been transplanted becomes a fibrous soft tissue due to infiltration of inflammation or infiltration of blood vessels.

An object of the invention is to provide a cartilage regenerative material that suppresses infiltration of fibrous soft tissue and brings about satisfactory cartilage regeneration. Another object of the invention is to provide a method for producing the cartilage regenerative material described above.

The inventors of the present invention conducted a thorough investigation in order to solve the problems described above, and as a result, the inventors found that in regard to a cartilage regenerative material including a porous body of a biocompatible polymer and a biocompatible polymer film, in a case in which the porous body contains chondrocytes and cartilage matrix, and the cartilage matrix exists in a region occupying 10% or more of a region extending from the surface of the transplant face of the porous body to a depth of 150 μm along the thickness, infiltration of fibrous soft tissue can be suppressed, and also, satisfactory cartilage regeneration is brought about. The invention was completed based on these findings.

That is, according to the invention, the following inventions are provided.

(1) A cartilage regenerative material comprising a porous body of a biocompatible polymer and a biocompatible polymer film, in which the porous body contains chondrocytes and cartilage matrix, and the cartilage matrix exists in a region occupying 10% or more of a region extending from the surface of the transplant face of the porous body to a depth of 150 μm along the thickness.

(2) The cartilage regenerative material according to (1), in which the cartilage matrix exists in a region occupying 20% or more of a region extending from the surface of the transplant face of the porous body to a depth of 150 μm along the thickness.

(3) The cartilage regenerative material according to (1) or (2), in which the biocompatible polymer of the porous body is a recombinant peptide or a chemically synthesized peptide.

(4) The cartilage regenerative material according to any one of (1) to (3), in which the biocompatible polymer of the porous body is a recombinant gelatin or a chemically synthesized gelatin.

(5) The cartilage regenerative material according to (4), in which the recombinant gelatin or the chemically synthesized gelatin is represented by Formula 1,

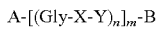
$$A-[(Gly-X-Y)_n]_m-B \quad \text{Formula 1:}$$

in Formula 1, n units of X each independently represent any amino acid residue; n units of Y each independently represent any amino acid residue; m represents an integer from 2 to 10; n represents an integer from 3 to 100; A represents an arbitrary amino acid residue or amino acid sequence; and B represents an arbitrary amino acid residue or amino acid sequence.

(6) The cartilage regenerative material according to (4) or (5), in which the recombinant gelatin or the chemically synthesized gelatin is any one of the following:

a peptide comprising the amino acid sequence set forth in SEQ ID NO:1;

a peptide having biocompatibility and comprising an amino acid sequence obtained by modifying the amino acid sequence set forth in SEQ ID NO:1 by deletion, substitution or addition of one or several amino acid residues; and a peptide having biocompatibility and comprising an amino acid sequence having at least 80% sequence identity with the amino acid sequence set forth in SEQ ID NO:1.

(7) The cartilage regenerative material according to any one of (1) to (6), in which the porous body is obtainable by freeze-drying an aqueous solution containing a biocompatible polymer.

(8) The cartilage regenerative material according to any one of (1) to (7), in which the biocompatible polymer film is a film for isolating a portion or the entirety of the transplant face of the porous body from the site of transplantation.

(9) The cartilage regenerative material according to any one of (1) to (8), in which the biocompatible polymer of the biocompatible polymer film is a recombinant gelatin or a chemically synthesized gelatin.

(10) The cartilage regenerative material according to (9), in which the biocompatible polymer of the biocompatible polymer film is represented by Formula 1,

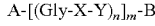
$$A-[(Gly-X-Y)_n]_m-B \quad \text{Formula 1:}$$

in Formula 1, n units of X each independently represent any amino acid residue; n units of Y each independently represent any amino acid residue; m represents an integer from 2 to 10; n represents an integer from 3 to 100; A represents an arbitrary amino acid residue or amino acid sequence; and B represents an arbitrary amino acid residue or amino acid sequence.

(11) The cartilage regenerative material according to (9) or (10), in which the biocompatible polymer of the biocompatible polymer film is any one of the following:

a peptide comprising the amino acid sequence set forth in SEQ ID NO:1;

a peptide having biocompatibility and comprising an amino acid sequence obtained by modifying the amino acid sequence set forth in SEQ ID NO:1 by deletion, substitution or addition of one or several amino acid residues; and a peptide having biocompatibility and comprising an amino acid sequence having at least 80% sequence identity with the amino acid sequence set forth in SEQ ID NO:1.

(12) The cartilage regenerative material according to any one of (1) to (11), in which the biocompatible polymer of the biocompatible polymer film has a degree of crosslinking of 4 to 15.

(13) The cartilage regenerative material according to any one of (1) to (12), in which the biocompatible polymer of the biocompatible polymer film has a degree of crosslinking of 4 to 8.

(14) The cartilage regenerative material according to any one of (1) to (13), in which the rate of decomposition, which is represented by Formula 4, of the biocompatible polymer of the biocompatible polymer film is 0.1 to 20 mass %/hour, $$\text{Rate of decomposition}=((W-We)-wo)/wo/T \quad \text{Formula 4:}$$

in Formula 4, W represents the mass of a tube containing a sample, which is recorded after decomposition by a collagenase and freeze-drying; We represents the blank mass of the tube that has been recorded in advance; wo represents the actual amount of addition of the sample; and T represents the time taken for shaking in a collagenase solution.

(15) The cartilage regenerative material according to any one of (1) to (14), in which the rate of decomposition, which is represented by Formula 4, of the biocompatible polymer of the biocompatible polymer film is 5 to 10 mass %/hour, $$\text{Rate of decomposition}=((W-We)-wo)/wo/T \quad \text{Formula 4:}$$

in Formula 4, W represents the mass of a tube containing a sample, which is recorded after decomposition by a collagenase and freeze-drying; We represents the blank mass of the tube that has been recorded in advance; wo represents the actual amount of addition of the sample; and T represents the time taken for shaking in a collagenase solution.

(16) The cartilage regenerative material according to any one of (1) to (15), in which the chondrocytes are at least one type of chondrocytes selected from the group consisting of articular cartilage-derived chondrocytes, auricular cartilage-derived chondrocytes, nasal cartilage-derived chondrocytes, iPS cell-derived chondrocytes, ES cell-derived chondrocytes, mesenchymal stem cell-derived chondrocytes, and chondrocytes obtained by a direct reprogramming method.

(17) The cartilage regenerative material according to any one of (1) to (16), in which the cartilage matrix exists in a region occupying 10% or more of a region extending from the surface of the articular cavity face of the porous body to a depth of 150 μm along the thickness.

(18) The cartilage regenerative material according to any one of (1) to (17), further comprising a pin of a biocompatible polymer.

(19) A method for producing a cartilage regenerative material being the cartilage regenerative material according to any one of (1) to (17), the method comprising:

Step A of freeze-drying an aqueous solution containing a biocompatible polymer and obtaining a porous body;

Step B of inoculating chondrocytes into the porous body obtained in Step A and culturing the chondrocytes; and Step C of providing a biocompatible polymer film.

(20) The method for producing a cartilage regenerative material according to (19), in which in Step A, a porous body is obtained by stirring the aqueous solution containing a biocompatible polymer and then freeze-drying the aqueous solution.

(21) A cartilage regenerative material for use in the treatment of cartilage regeneration, the cartilage regenerative material comprising a porous body of a biocompatible polymer and a biocompatible polymer film, in which the porous body contains chondrocytes and cartilage matrix, and the cartilage matrix exists in a region occupying 10% or more of a region extending from the surface of the transplant face of the porous body to a depth of 150 μm along the thickness.

(22) A method for regenerating cartilage, the method comprising a step of transplanting a cartilage regenerative material to a patient in need of cartilage regeneration, the cartilage regenerative material including a porous body of a biocompatible polymer and a biocompatible polymer film, in which the porous body contains chondrocytes and cartilage matrix, and the cartilage matrix exists in a region occupying 10% or more of a region extending from the surface of the transplant face of the porous body to a depth of 150 μm along the thickness.

(23) Use of a porous body of a biocompatible polymer and a biocompatible polymer film for the production of a cartilage regenerative material, in which the porous body contains chondrocytes and cartilage matrix, and the cartilage matrix exists in a region occupying 10% or more of a region extending from the surface of a transplant face of the porous body to a depth of 150 μm along the thickness.

The cartilage regenerative material of the invention suppresses infiltration of fibrous soft tissue, brings about satisfactory cartilage regeneration, and is useful for cell transplantation therapy. According to the method for producing a cartilage regenerative material of the invention, the cartilage regenerative material of the invention that suppresses the infiltration of fibrous soft tissue described above and brings about satisfactory cartilage regeneration can be produced.

DESCRIPTION OF THE PREFERRED EMBODIMENTS

Figure 1:
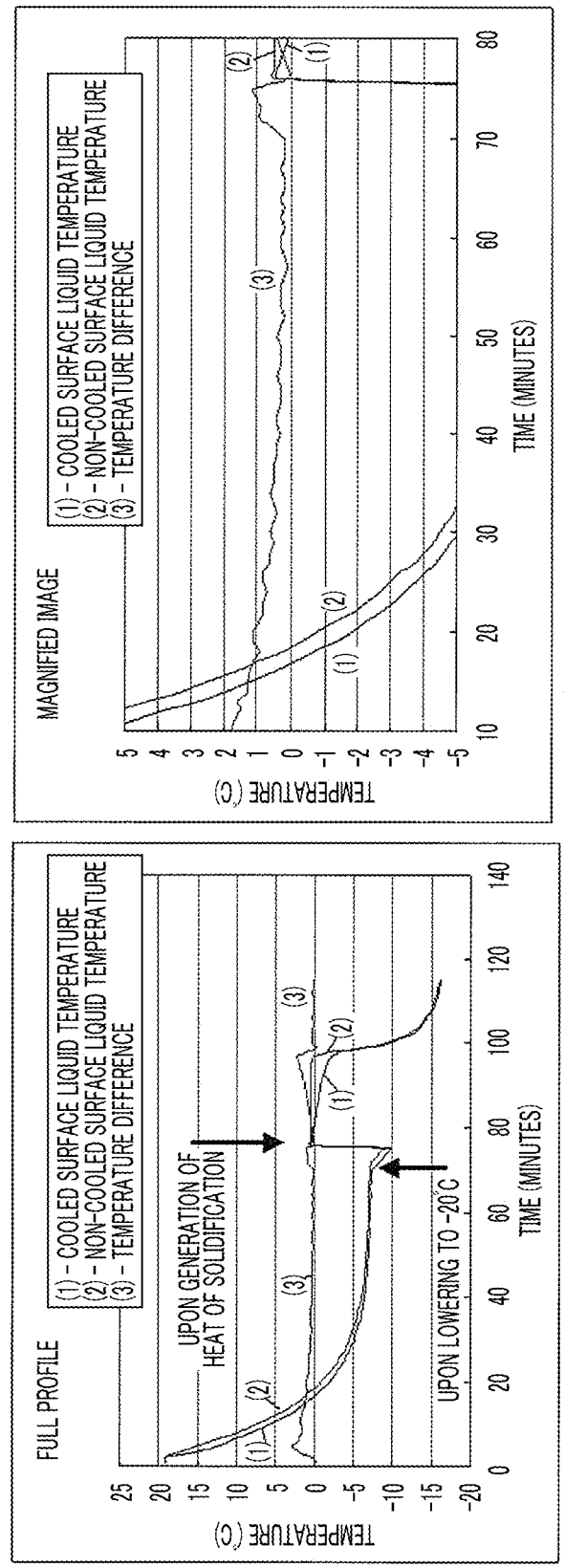
FIG. 1 illustrates a liquid temperature profile obtained under Condition A.

Hereinafter, embodiments of the invention will be explained in detail.

The cartilage regenerative material of the invention comprises a porous body of a biocompatible polymer and a biocompatible polymer film, in which the porous body contains chondrocytes and cartilage matrix, and the cartilage matrix exists in a region occupying 10% or more of a region extending from the surface of a transplant face of the porous body to a depth of 150 μm along the thickness.

The cartilage regenerative material of the invention suppresses infiltration of fibrous soft tissue and brings about satisfactory cartilage regeneration, and therefore, the cartilage regenerative material can be used for cartilage regeneration. The cartilage regenerative material of the invention can be used as, for example, a transplant material to be transplanted to a cartilage defect site.

It is a completely unexpected remarkable effect that the cartilage regenerative material of the invention comprising a porous body of a biocompatible polymer and a biocompatible polymer film, in which the porous body contains chondrocytes and cartilage matrix, and the cartilage matrix exists in a region occupying 10% or more of a region extending from the surface of a transplant face of the porous body to a depth of 150 μm along the thickness, suppresses infiltration of fibrous soft tissue and brings about satisfactory cartilage regeneration as described above. In WO2011/108537A, description on bone regeneration is given; however, no investigation was conducted on cartilage regeneration. Bone regeneration and cartilage regeneration are different phenomena, and cartilage regeneration action cannot be predicted from bone regeneration action. Also, in JP2001-519210A, the feature of the invention that cartilage matrix exists in a region occupying 10% or more of a region extending from the surface of a transplant face of a porous body to a depth of 150 μm along the thickness, is neither described nor suggested. JP2001-519210A suggests nothing about the possibility of achieving an effect that infiltration of fibrous soft tissue is suppressed and satisfactory cartilage regeneration is brought about as a result of the above-described feature.

In the cartilage regenerative material of the invention, the cartilage matrix exists in a region occupying 10% or more (preferably 20% or more, and more preferably 30% or more) of a region extending from the surface of a transplant face of a porous body to a depth of 150 μm along the thickness. The proportion of the region in which the cartilage matrix exists in the region extending from the surface of a transplant face of the porous body to a depth of 150 μm along the thickness, is referred to as "cartilage matrix filling proportion" in the present specification. As described above, by adjusting the cartilage matrix filling proportion on the transplant face side to be 10% or higher, the cartilage regenerative material of the invention is enabled to suppress infiltration of fibrous soft tissue and bring about satisfactory cartilage regeneration. The upper limit of the cartilage matrix filling proportion on the transplant face side is not particularly limited, and the upper limit may be 100%, or may be less than 100%.

Preferably, in the cartilage regenerative material of the invention, cartilage matrix exists in a region of 10% or more (more preferably 20% or more, even more preferably 30% or more, and still more preferably 50% or more) of a region extending from the surface of the articular cavity face of the porous body to a depth of 150 µm along the thickness. The upper limit of the cartilage matrix filling proportion on the articular cavity face side is not particularly limited, and the upper limit may be 100%, or may be less than 100%.

Figure 19:
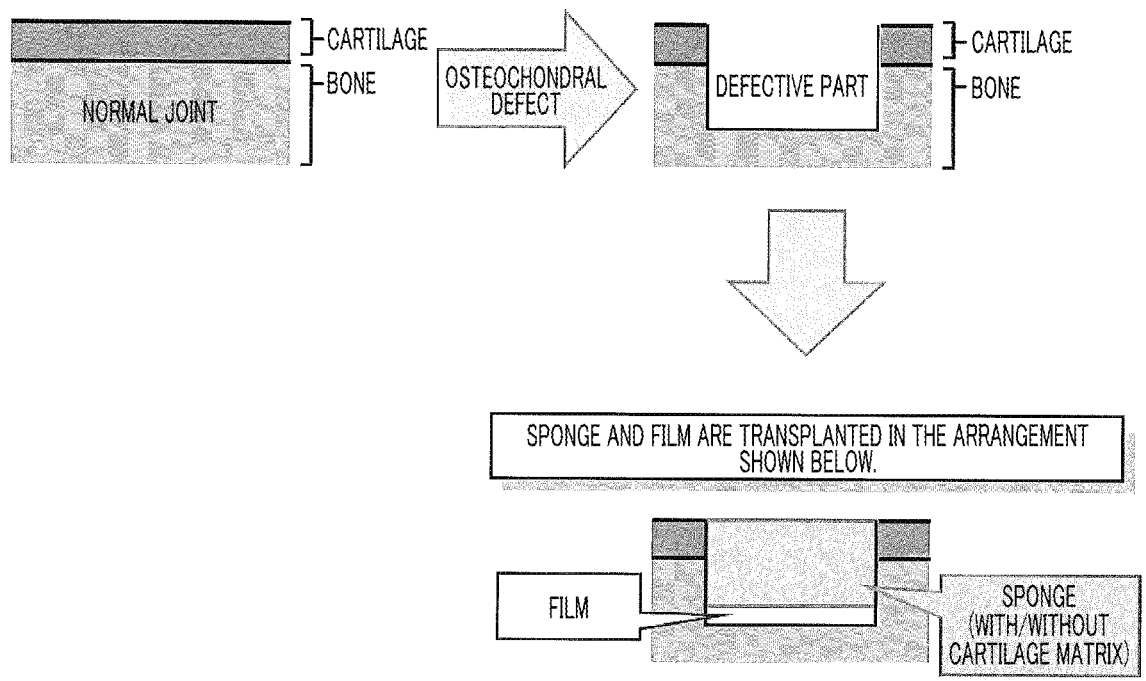
FIG. 19 shows the positional relation between a sponge and a film.

A transplant face of the porous body means the face on the side that is brought into contact with the defect part in vivo (in the case of the sponge of FIG. 19, the lower surface), and the articular cavity face of the porous body means the face on the opposite side of the transplant face (in the case of the sponge of FIG. 19, the upper surface).

Measurement of the cartilage matrix filling proportion can be carried out according to the method described in "[14] Evaluation of samples having different cartilage matrix filling proportions of bottom face" in the Examples of the present specification. That is, slices of a porous body are produced (formalin fixation and paraffin embedment), and cross-sections are visualized by performing safranin O staining. Thus, evaluation is carried out. That is, attention was paid to a thickness of 150 µm from the surface of the transplant face (bottom face) or the articular cavity face (face on the opposite side of the transplant face) of the stained tissue slices, and the area of a region that was positive for safranin O staining was measured. By determining the proportion of the area of the safranin O staining positive region with respect to the total area of the region from the surface to a depth of 150 µm, the cartilage matrix filling proportion in the 150-µm layer can be determined.

Hereinafter, the constituent elements of the invention will be explained.

(1) Porous Body of Biocompatible Polymer

The porous body used in the invention is constructed from a biocompatible polymer.

(1-1) Biocompatible Polymer

Biocompatibility means that in a case in which the material is brought into contact with a living body, the material does not give a rise to a noticeably harmful reaction such as a long-term and chronic inflammation reaction. Whether the biocompatible polymer used in the invention is decomposed in vivo is not particularly limited, as long as the polymer has biocompatibility; however, it is preferable that the polymer is a biodegradable polymer. Specific examples of a non-biodegradable polymer include polytetrafluoroethylene (PTFE), polyurethane, polypropylene, polyester, vinyl chloride, polycarbonate, acryl, stainless steel, titanium, silicone, and MPC (2-methacryloyloxyethylphosphorylcholine). Specific examples of a biodegradable polymer include polypeptides such as a recombinant peptide and a chemically synthesized peptide (for example, gelatin that will be explained below), polylactic acid, polyglycolic acid, a lactic acid-glycolic acid copolymer (PLGA), hyaluronic acid, glycosaminoglycan, proteoglycan, chondroitin, cellulose, agarose, carboxymethyl cellulose, chitin, and chitosan. Among the compounds described above, a recombinant peptide is particularly preferred. These biocompatible polymers may be devised in order to increase the cell adhesiveness. Specifically, methods such as "coating of a base material surface with a cell adhesion matrix (fibronectin, vitronectin, or laminin) or a cell adhesion sequence (an ROD sequence, a LDV sequence, a REDV sequence (SEQ ID NO: 2), a YIGSR sequence (SEQ ID NO: 3), a PDSGR sequence (SEQ ID NO: 4), a RYVVLPR sequence (SEQ ID NO: 5), a LGTIPG sequence (SEQ ID NO: 6), a RNIAEIIKDI sequence (SEQ ID NO: 7), an IKVAV sequence (SEQ ID NO: 8), a LRE sequence, a DGEA sequence (SEQ ID NO: 9), or a HAV sequence; all indicated by one-letter codes of amino acids) peptide", "amination or cationization of the base material surface", or "hydrophilic treatment of the base material surface by a plasma treatment or corona discharge" can be used.

The type of the polypeptide such as a recombinant peptide or a chemically synthesized peptide is not particularly limited as long as the polypeptide has biocompatibility; however, for example, gelatin, collagen, elastin, fibronectin, pronectin, laminin, tenascin, fibrin, fibroin, entactin, thrombospondin, and retronectin are preferred, while gelatin, collagen, and atelocollagen are most preferred. Gelatin that is intended to be used in the invention is preferably naturally occurring gelatin, a recombinant gelatin, or a chemically synthesized gelatin, and more preferred is a recombinant gelatin. The term naturally occurring gelatin as used herein means a gelatin produced from naturally occurring collagen.

The term chemically synthesized peptide or chemically synthesized gelatin means a peptide or gelatin that has been artificially synthesized. Synthesis of a peptide such as gelatin may be solid-phase synthesis or liquid-phase synthesis; however, solid-phase synthesis is preferred. Solid-phase synthesis of peptides is well known to those ordinarily skilled in the art, and examples include a Fmoc group synthesis method of using a Fmoc group (Fluorenyl-Methoxy-Carbonyl group) as a protective group for an amino group; and a Boc group synthesis method of using a Boc group (tert-ButylOxyCarbonyl group) as a protective group for an amino group. Regarding preferred embodiments of the chemically synthesized gelatin, the matters described in section (1-3) Recombinant gelatin given below in the present specification can be applied.

Recombinant gelatin will be explained below in the present specification.

The hydrophilicity value "1/IOB" value of the biocompatible polymer used in the invention is preferably from 0 to 1.0. The hydrophilicity value is more preferably from 0 to 0.6, and even more preferably from 0 to 0.4. IOB is an index of hydrophilicity/hydrophobicity based on an organic conceptual diagram showing the polarity/non-polarity of organic compounds suggested by FUJITA, Atsushi, and the details thereof are explained in, for example, "Pharmaceutical Bulletin", Vol. 2, 2, pp. 163-173 (1954), "Kagaku no Ryoiki (Domain of Chemistry)", Vol. 11, 10, pp. 719-725 (1957), and "Fragrance Journal", Vol. 50, pp. 79-82 (1981). To describe briefly, the root of all organic compounds is considered to be methane ($CH_4$), and other compounds are all regarded as derivatives of methane. Certain values are set respectively for the number of carbon atoms, substituents, modified parts, rings, and the like of the compounds, and the scores are added to determine the organic values (OV) and the inorganic values (IV). These values are plotted on a graph, with the X-axis representing the organic values and the Y-axis representing the inorganic values. The IOB in the organic conceptual diagram means the ratio of the inorganic value (IV) with respect to the organic value (OV) in the organic conceptual diagram, that is, "inorganic value (IV)/ organic value (OV)". Regarding the details of the organic conceptual diagram, reference can be made to "Shinpan Yuki Gainenzu—Kiso to Oyo—(New Edition Organic Conceptual Diagram—Fundamentals and Applications—)" (written by KODA, Yoshio, et al., Sankyo Shuppan Co., Ltd., 2008). In the present specification, hydrophilicity and hydrophobicity is indicated with the "1/IOB" value, which is the reciprocal of IOB. As the "1/IOB" value is smaller (closer to 0), this indicates that the compound is hydrophilic.

By adjusting the "1/IOB" value of the biocompatible polymer used in the invention to the range described above, the biocompatible polymer has higher hydrophilicity and has enhanced water absorbing properties. Accordingly, it is speculated that the high hydrophilicity acts effectively on the retention of nutrient components.

In a case in which the biocompatible polymer used in the invention is a polypeptide, the hydrophilicity/hydrophobicity index represented by the Grand average of hydropathicity (GRAVY) value of the polypeptide is preferably 0.3 or lower and −9.0 or higher, and more preferably 0.0 or lower and −7.0 or higher. The Grand average of hydropathicity (GRAVY) value can be obtained by the method described in "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

By adjusting the GRAVY value of the biocompatible polymer used in the invention to the range described above, the biocompatible polymer has higher hydrophilicity and has enhanced water absorbing properties. Accordingly, it is speculated that the high hydrophilicity acts effectively on the retention of nutrient components.

(1-2) Crosslinking

The biocompatible polymer used in the invention may be a crosslinked polymer, or may be a polymer that is not crosslinked; however, a crosslinked polymer is preferred. By using a crosslinked biocompatible polymer, there is obtained an effect that in a case in which the cartilage regenerative material of the invention is cultured in a medium, and in a case in which the cartilage regenerative material is transplanted into a living body, the cartilage regenerative material being instantaneously decomposed is prevented. Regarding general crosslinking methods, thermal crosslinking, crosslinking by means of an aldehyde (for example, formaldehyde or glutaraldehyde), crosslinking by means of a condensing agent (carbodiimide, cyanamide, or the like), enzymatic crosslinking, photocrosslinking, ultraviolet crosslinking, hydrophobic interaction, hydrogen bonding, ionic interaction, and the like are known. The crosslinking method used in the invention is preferably thermal crosslinking, ultraviolet crosslinking, or enzymatic crosslinking, and particularly preferably thermal crosslinking.

In a case in which enzyme-induced crosslinking is carried out, the enzyme is not particularly limited as long as the enzyme has an effect of crosslinking between polymer molecules; however, preferably a transglutaminase and a laccase, and most preferably a transglutaminase, can be used. There are no particular limitations on specific examples of the polymer that is enzymatically crosslinked by a transglutaminase as long as the polymer is a protein having a lysine residue and a glutamine residue. The transglutaminase may be a mammal-derived enzyme or a microbially derived enzyme, and specifically, ACTIVA series manufactured by Ajinomoto Co., Inc., and mammal-derived transglutaminases that are released as reagents, for example, Guinea pig liver-derived transglutaminase, goat-derived transglutaminase, and rabbit-derived transglutaminase, which are products of Oriental Yeast Co., Ltd.; Upstate USA, Inc.; Biodesign International, Inc.; and the like, and human-derived blood coagulation factor (Factor XIIIa, Haematologic Technologies, Inc.).

The reaction temperature in the case of performing crosslinking (for example, thermal crosslinking) is not particularly limited as long as crosslinking is enabled; however, the reaction temperature is preferably −100° C. to 500° C., more preferably 0° C. to 300° C., even more preferably 50° C. to 300° C., still more preferably 100° C. to 250° C., and even more preferably 120° C. to 200° C.

(1-3) Recombinant Gelatin

The recombinant gelatin as used herein means a polypeptide or protein-like substance having an amino acid sequence similar to that of gelatin, which is produced by a gene recombination technology. It is preferable that the recombinant gelatin that can be used in the invention has repeats of a sequence represented by Gly-X-Y (where X and Y each independently represent any amino acid residue), which is characteristic to collagen. Here, a plurality of the Gly-X-Y sequences may be identical to or different from one another. Preferably, two or more sequences of cell adhesion signals are included in one molecule. Regarding the recombinant gelatin that is used in the invention, a recombinant gelatin having an amino acid sequence derived from a partial amino acid sequence of collagen can be used. For example, the recombinant gelatins described in EP1014176B, U.S. Pat. No. 6,992,172B, WO2004/85473A, and WO2008/103041A can be used; however, the examples are not limited to these. Preferred examples of the recombinant gelatin that is used in the invention are recombinant gelatins of the following embodiments.

A recombinant gelatin has the original properties of naturally occurring gelatin and thus has excellent biocompatibility. Also, since it is not a substance derived from a natural source, a recombinant gelatin has no risk of bovine spongiform encephalopathy (BSE) or the like, and has an excellent characteristic of being non-infectious. Since a recombinant gelatin is homogeneous compared to naturally occurring gelatin and has a predetermined sequence, it is possible to precisely design a recombinant gelatin with fewer fluctuations, in connection with strength and degradability, through crosslinking or the like.

The molecular weight of the recombinant gelatin is not particularly limited; however, the molecular weight is preferably from 2,000 to 100,000 (from 2 kDa to 100 kDa), more preferably from 2,500 to 95,000 (from 2.5 kDa to 95 kDa), even more preferably from 5,000 to 90,000 (from 5 kDa to 90 kDa), and most preferably from 10,000 to 90,000 (from 10 kDa to 90 kDa).

It is preferable that the recombinant gelatin has repeats of a sequence represented by Gly-X-Y, which is characteristic to collagen. Here, a plurality of the Gly-X-Y sequences may be identical to or different from one another. In regard to the sequence Gly-X-Y, Gly represents glycine, and X and Y each represent an arbitrary amino acid (preferably, any arbitrary amino acid other than glycine). The sequence represented by Gly-X-Y characteristic to collagen is a highly specific partial structure present in the amino acid compositions and sequences of gelatin and collagen, compared to other proteins. In this partial structure, glycine accounts for about one-third of the whole composition, and in the amino acid sequence, glycine repeatedly appears at a rate of one in every three amino acid residues. Glycine is the simplest amino acid, and there are fewer restrictions to the arrangement in a molecular chain. Thus, glycine greatly contributes to regeneration of the helix structure in the case of gelation. It is preferable that the amino acids represented by X and Y include a large proportion of imino acids (proline and oxyproline), and imino acids account for 10% to 45% of the total amount of the amino acids. Preferably, amino acids that account for 80% or more, more preferably 95% or more, and most preferably 99% or more, of the sequence of the recombinant gelatin, constitute the repeating structure of Gly-X-Y.

In general gelatins, polar amino acids that have an electric charge and polar amino acids that are uncharged exist at a ratio of 1:1. Here, the term polar amino acid specifically refers to cysteine, aspartic acid, glutamic acid, histidine, lysine, asparagine, glutamine, serine, threonine, tyrosine, or arginine, and among these, polar uncharged amino acids include cysteine, asparagine, glutamine, serine, threonine, and tyrosine. In regard to the recombinant gelatin used in the invention, the proportion of polar amino acids among all the amino acids that constitute the recombinant gelatin is 10% to 40%, and preferably 20% to 30%. Meanwhile, the proportion of uncharged amino acids in the polar amino acids is preferably 5% or more and less than 20%, and more preferably 5% or more and less than 10%. It is also preferable that any one amino acid, and preferably 2 or more amino acids, of serine, threonine, asparagine, tyrosine, and cysteine are not included in the amino acid sequence.

Generally, in regard to polypeptides, minimal amino acid sequences that function as cell adhesion signal sequences are known (for example, "Byotai Seiri (Pathophysiology)", Vol. 9, No. 7 (1990), p. 527, published by Nagai Shoten Co., Ltd.). It is preferable that the recombinant gelatin used in the invention contains two or more such minimal amino acid sequences that function as cell adhesion signals in one molecule. Regarding specific sequences, from the viewpoint of being applicable to many kinds of adhering cells, an RGD sequence, a LDV sequence, a REDV sequence (SEQ ID NO: 2), a YIGSR sequence (SEQ ID NO: 3), a PDSGR sequence (SEQ ID NO: 4), a RYVVLPR sequence (SEQ ID NO: 5), a LGTIPG sequence (SEQ ID NO: 6), a RNIAEIIKDI sequence (SEQ ID NO: 7), an IKVAV sequence (SEQ ID NO: 8), a LRE sequence, a DGEA sequence (SEQ ID NO: 9), and a HAV sequence, which are expressed in one-letter codes of amino acids, are preferred. More preferred sequences include an RGD sequence, a YIGSR sequence (SEQ ID NO: 3), a PDSGR sequence (SEQ ID NO: 4), a LGTIPG sequence (SEQ ID NO: 6), an IKVAV sequence (SEQ ID NO: 8), and a HAV sequence, and particularly preferred is an RGD sequence. Among RGD sequences, an ERGD sequence (SEQ ID NO: 10) is preferred. When a recombinant gelatin having cell adhesion signal sequences is used, the amount of cell matrix production can be increased. For example, in a case in which mesenchymal stem cells are used as cells, the production of glycosaminoglycans (GAG) in chondrocyte differentiation can be increased.

In regard to the disposition of RGD sequences in the recombinant gelatin used in the invention, it is preferable that the number of amino acids between RGD sequences is between 0 and 100, and preferably between 25 and 60, and is not uniform.

The content of these minimal amino acid sequences is preferably 3 to 50, more preferably 4 to 30, even more preferably 5 to 20, and most preferably 12, in one molecule of protein, from the viewpoints of cell adhesion and proliferation properties.

In regard to the recombinant gelatin used in the invention, the proportion of the RGD sequences (motifs) with respect to the total number of amino acid residues is preferably at least 0.4%. In a case in which a recombinant gelatin includes 350 or more amino acid residues, it is preferable that each stretch of 350 amino acid residues includes at least one RGD motif. The proportion of the RGD motif with respect to the total number of amino acid residues is more preferably at least 0.6%, even more preferably at least 0.8%, still more preferably at least 1.0%, even more preferably at least 1.2%, and most preferably at least 1.5%. The number of RGD motifs within a recombinant peptide is preferably at least 4, more preferably at least 6, even more preferably at least 8, still more preferably from 12 to 16, per 250 amino acid residues. The proportion of 0.4% of the RGD motifs corresponds to at least one RGD sequence per 250 amino acid residues. Since the number of the RGD motifs is an integer, in order to satisfy the characteristic requirement of 0.4%, a gelatin molecule containing 251 amino acid residues must include at least two RGD sequences. Preferably, the recombinant gelatin of the invention includes at least two RGD sequences per 250 amino acid residues; more preferably includes at least three RGD sequences per 250 amino acid residues; and even more preferably includes at least four RGD sequences per 250 amino acid residues. According to another embodiment of the recombinant gelatin of the invention, the recombinant gelatin includes at least four RGD motifs, preferably at least six RGD motifs, more preferably at least eight RGD motifs, and still more preferably from 12 to 16 RGD motifs.

The recombinant gelatin may be partially hydrolyzed.

Preferably, the recombinant gelatin used in the invention is represented by Formula 1: A-[(Gly-X-Y)$_n$]$_m$-B. n units of X each independently represent any one amino acid residue, and n units of Y each independently represent any one amino acid residue. m represents an integer from 2 to 10, and preferably 3 to 5. n represents an integer from 3 to 100, preferably 15 to 70, and more preferably 50 to 65. A represents an arbitrary amino acid residue or amino acid sequence, and B represents an arbitrary amino acid residue or amino acid sequence.

More preferably, the recombinant gelatin used in the invention is represented by formula: Gly-Ala-Pro-[(Gly-X-Y)$_{63}$]$_3$-Gly (SEQ ID NO: 11)(in the formula, 63 units of X each independently represent any one amino acid residue; 63 units of Y each independently represent any one amino acid residue; and 63 units of Gly-X-Y may be identical to or different from one another).

It is preferable that a plurality of the sequence units of naturally occurring collagen are bonded to the repeating unit. The naturally occurring collagen as used herein may be any collagen substance that exists in nature; however, the collagen is preferably type I, type II, type III, type IV, or type V collagen. The collagen is more preferably type I, type II, or type III collagen. According to another embodiment, the source of the above-mentioned collagens is preferably human, cow, pig, mouse, or rat, and more preferably a human source.

The isoelectric point of the recombinant gelatin used in the invention is preferably 5 to 10, more preferably 6 to 10, and even more preferably 7 to 9.5.

Preferably, the recombinant gelatin is not deaminated.

Preferably, the recombinant gelatin does not have a telopeptide.

Preferably, the recombinant gelatin is a substantially pure polypeptide produced from a nucleic acid that encodes an amino acid sequence.

The recombinant gelatin used in the invention is particularly preferably:

(1) a peptide comprising the amino acid sequence set forth in SEQ ID NO:1;

(2) a peptide having biocompatibility and comprising an amino acid sequence obtained by modifying the amino acid sequence set forth in SEQ ID NO:1 by deletion, substitution or addition of one or several amino acid residues; or (3) a peptide having biocompatibility and comprising an amino acid sequence having at least 80% (preferably at least 90%, more preferably at least 95%, and most preferably at least 98%) sequence identity with the amino acid sequence set forth in SEQ ID NO:1.

The term "one or several" in the phrase "amino acid sequence obtained by modifying . . . by deletion, substitution or addition of one or several amino acid residues" means preferably 1 to 20, more preferably 1 to 10, even more preferably 1 to 5, and particularly preferably 1 to 3.

The recombinant gelatin used in the invention can be produced by a gene recombination technology that is known to those ordinarily skilled in the art, and the recombinant gelatin can be produced according to the methods described in, for example, EP1014176A2, U.S. Pat. No. 6,992,172B, WO2004/85473A, and WO2008/103041A. Specifically, a gene that encodes the amino acid sequence of a predetermined recombinant gelatin is obtained, this is incorporated into an expression vector to produce a recombinant expression vector, and this is introduced into an appropriate host. Thus, a transformant is produced. The transformant thus obtained is cultured in an appropriate medium, and thereby, a recombinant gelatin is produced. Then, the recombinant gelatin thus produced is collected from the culture product. Thereby, the recombinant gelatin used in the invention can be produced.

(1-4) Method for Producing Porous Body of Biocompatible Polymer

The method for producing a porous body of a biocompatible polymer is not particularly limited; however, for example, a porous body of a biocompatible polymer can be obtained by freeze-drying an aqueous solution including a biocompatible polymer. As an example of the method for producing a porous body of a biocompatible polymer, there may be mentioned a production method including:

(a) a step of cooling a solution of a biocompatible polymer to an unfrozen state at a temperature at which the difference between the temperature of a part having the highest liquid temperature in the solution and the temperature of a part having the lowest liquid temperature in the solution is 2.5° C. or less, and the temperature of the part having the highest liquid temperature in the solution is lower than or equal to the melting point of the solvent;

(b) a step of freezing the solution in an unfrozen state of the biocompatible polymer obtained in Step (a); and (c) a step of freeze-drying the frozen solution of the biocompatible polymer obtained in Step (b).

In a case in which the biocompatible polymer solution is cooled to an unfrozen state, as the difference between the temperature of a part having the highest liquid temperature in the solution and the temperature of a part having the lowest liquid temperature in the solution is adjusted to be 2.5° C. or less (preferably 2.3° C. or less, and more preferably 2.1° C. or less), that is, as the difference in temperature is adjusted to be smaller, the difference in the size of the pores in the porous body thus obtainable is made smaller.

The lower limit of the difference between the temperature of a part having the highest liquid temperature in the solution and the temperature of a part having the lowest liquid temperature in the solution is not particularly limited, and the temperature difference may be 0° C. or more, and for example, may be 0.1° C. or more, 0.5° C. or more, 0.8° C. or more, or 0.9° C. or more. A porous body produced thereby can achieve a superior cartilage regeneration effect.

In regard to the cooling of Step (a), it is preferable to perform cooling by means of, for example, a material having a thermal conductivity lower than that of water (preferably, TEFLON (registered trademark)), and the part having the highest liquid temperature in the solution can be assumed to be a part remotest from the cooling surface, and the part having the lowest liquid temperature in the solution can be assumed to be the liquid temperature at the cooling surface.

Preferably, in Step (a), the difference between the temperature of a part having the highest liquid temperature in the solution and the temperature of a part having the lowest liquid temperature in the solution immediately before the generation of the heat of solidification is 2.5° C. or less, more preferably 2.3° C. or less, and even more preferably 2.1° C. or less. Here, the "temperature difference immediately before the generation of the heat of solidification" means the temperature difference at the time when the temperature difference becomes the largest in a time period between 1 second and 10 seconds before the generation of the heat of solidification.

Preferably, in Step (a), the temperature of a part having the lowest liquid temperature in the solution is (melting point of the solvent—5° C.) or lower, more preferably (melting point of the solvent—5° C.) or lower and (melting point of the solvent—20° C.) or higher, and even more preferably (melting point of the solvent—6° C.) or lower and (melting point of the solvent—16° C.) or higher. The solvent of the "melting point of the solvent" is the solvent of the solution of the biocompatible polymer.

In Step (b), the solution of the biocompatible polymer in an unfrozen state obtained in Step (a) is frozen. The cooling temperature for freezing in Step (b) is not particularly limited and may vary depending on the cooling equipment. Preferably, the cooling temperature is a temperature lower by 3° C. to 30° C., more preferably a temperature lower by 5° C. to 25° C., and even more preferably a temperature lower by 10° C. to 20° C., than the temperature of the part having the lowest liquid temperature in the solution.

In Step (c), the frozen solution of the biocompatible polymer obtained in Step (b) is freeze-dried. Freeze-drying can be carried out by a conventional method, and for example, freeze-drying can be carried out by performing vacuum drying at a temperature lower than the melting point of the solvent, and further performing vacuum drying at room temperature (20° C.).

The shape and size of the porous body of the biocompatible polymer are not particularly limited, and a porous body having an appropriate shape and an appropriate size for the purpose of use can be used. Examples of the shape include, but are not particularly limited to, a cylinder and a cuboid, and any shape that coincides with the shape of the defect part, which is an affected part, can be employed. The size of the cylinder is preferably such that the diameter is 2 mm to 2 cm, and the height (thickness) is 1 mm to 2 cm. The size of the cuboid is preferably such that the longitudinal length and the horizontal length are 2 mm to 2 cm, and the height (thickness) is 1 mm to 2 cm.

The average pore size of the porous body of the biocompatible polymer is not particularly limited; however, the average pore size is preferably 10 to 400 µm, more preferably 20 to 200 µm, even more preferably 30 to 100 µm, and particularly preferably 40 to 90 µm. The average pore size of the porous body can be measured according to the method described in "[8] Evaluation of pore size of recombinant peptide porous body" in the Examples.

(2) Chondrocytes and Cartilage Matrix

Regarding the chondrocytes used in the invention, any chondrocytes can be used as long the cells are capable of cell transplantation and exhibiting cartilage regenerative capacity, and the type of the cells is not particularly limited. Furthermore, one kind of chondrocytes may be used, or multiple kinds of chondrocytes may also be used in combination. Furthermore, the chondrocytes to be used are preferably animal cells, more preferably vertebrate-derived cells, and particularly preferably human-derived cells. Regarding the chondrocytes, at least one type of chondrocytes selected from the group consisting of articular cartilage-derived chondrocytes, auricular cartilage-derived chondrocytes, nasal cartilage-derived chondrocytes, induced pluripotent stem cell (iPS cell)-derived chondrocytes, embryonic stem cell (ES cell)-derived chondrocytes, mesenchymal stem cell (MSC)-derived chondrocytes, and chondrocytes obtained by a direct reprogramming method, can be used. A direct reprogramming method is a technique of directly changing cells such as fibroblasts extracted from the skin to chondrocytes. The origin of the cells may be any of autologous cells and heterologous cells.

Cartilage matrix means components produced by chondrocytes, and it is mainly extracellular matrix. Cartilage matrix includes glycosaminoglycans (GAG), chondroitin sulfate, and proteoglycans as main components, and depending on cases, cartilage matrix also includes collagenous fibers and elastic fibers. The presence of the cartilage matrix can be checked by safranin O staining.

The amount of use of chondrocytes with respect to the porous body of a biocompatible polymer is not particularly limited; however, the amount of use is preferably $1.0 \times 10^5$ cells/cm$^3$ to $1.0 \times 10^8$ cells/cm$^3$, more preferably $1.0 \times 10^6$ cells/cm$^3$ to $5.0 \times 10^7$ cells/cm$^3$, and even more preferably $2.0 \times 10^6$ cells/cm$^3$ to $1.0 \times 10^7$ cells/cm$^3$, per unit volume of the porous body of the biocompatible polymer. As the lower limit is adjusted to the range described above, the effects of the cells can be exhibited in a case in which the cells are used for transplantation applications, and as the upper limit is adjusted to the range described above, the components that may be optionally present inside the porous body of the biocompatible polymer can be supplied to the cells. Here, the components inside the porous body of a biocompatible polymer are not particularly limited; however, the components that are included in the medium that will be described below may be mentioned.

(3) Biocompatible Polymer Film

The cartilage regenerative material of the invention includes a biocompatible polymer film together with a porous body of a biocompatible polymer. That is, according to the invention, a porous body of a biocompatible polymer including chondrocytes and cartilage matrix is used in combination with a biocompatible polymer film.

The porous body of a biocompatible polymer and the biocompatible polymer film may be supplied separately in the form of kits, or the porous body of a biocompatible polymer and the biocompatible polymer film may also be supplied in the form of a product bonded together. Preferably, the porous body of a biocompatible polymer and the biocompatible polymer film are in the form of separate kits.

In a case in which the porous body of a biocompatible polymer and the biocompatible polymer film are supplied separately in the form of kits, the user may bond the porous body of a biocompatible polymer and the biocompatible polymer film together and then transplant the resultant. Alternatively, the use may transplant the biocompatible polymer film and then transplant the porous body of a biocompatible polymer.

It is preferable that the biocompatible polymer film is used as a film for isolating a portion or the entirety of the transplant face of the porous body of a biocompatible polymer from the site of transplantation. For example, it is preferable that the biocompatible polymer film is transplanted first onto the site of transplantation, and subsequently, the porous body of a biocompatible polymer is transplanted onto the top surface (surface on the opposite side of the surface that is in contact with the site of transplantation) of the biocompatible polymer film. Alternatively, in a case in which the porous body of a biocompatible polymer and the biocompatible polymer film are bonded together and then transplanted, it is preferable to transplant the biocompatible polymer film so as to be brought into direct contact with the site of transplantation.

Specific examples and preferred ranges of the biocompatible polymer that constitutes the biocompatible polymer film are the same as those in the case of the biocompatible polymer that constitutes the porous body of a biocompatible polymer, and specifically, the specific examples and the preferred ranges are as described in the above sections (1-1) Biocompatible polymer, (1-2) Crosslinking, and (1-3) Recombinant gelatin in the present specification. The biocompatible polymer that constitutes the biocompatible polymer film may be the same as, or may be different from, the biocompatible polymer that constitutes the porous body of a biocompatible polymer.

The method for producing a biocompatible polymer film is not particularly limited, and the production can be carried out by a conventional method. For example, a biocompatible polymer film can be produced by causing an aqueous solution of a biocompatible polymer to flow into a plastic tray, and drying the aqueous solution at low temperature (for example, in a refrigerator).

The biocompatible polymer film can be crosslinked. In a case in which the polymer film is crosslinked, the degree of crosslinking is not particularly limited; however, the degree of crosslinking is generally 4 to 15, more preferably 6 to 13, even more preferably 4 to 8, and particularly preferably 5 to 7. The degree of crosslinking is the number of crosslinks per molecule. Measurement of the degree of crosslinking can be carried out using the TNBS (2,4,6-trinitrobenzenesulfonic acid) method described in section [10] Method for measuring degree of crosslinking in the Examples.

The rate of decomposition of the biocompatible polymer film varies depending on the degree of crosslinking. The rate of decomposition of the biocompatible polymer film can be measured and evaluated by the method described below in section [11] Method for measuring rate of decomposition in the Examples.

Specifically, 5 mg of a sample (film) is introduced into a tube, the mass of which has been measured in advance, and the actual amount of addition is recorded. 2.5 mg of Actinomyces-derived collagenase is dissolved in 50 ml of phosphate buffered saline (PBS), and a collagenase solution is obtained. 1 ml of this collagenase solution is added to the tube containing the sample, and the content is mixed by vortexing. Subsequently, the mixture is shaken for a predetermined time (=T) at 37° C. Subsequently, the tube is centrifuged for 1 minute at 10,000 G, and the supernatant is removed using a pipette. 1 ml of ultrapure water is added to the tube, and the content is mixed by vortexing. Subsequently, the tube is centrifuged for 1 minute at 10,000 G, and the supernatant is removed using a pipette. This operation is repeated one more time. Subsequently, the sample is freeze-dried, and the mass of the tube containing the sample is recorded. The rate of decomposition of the film is calculated by the following formula (Formula 4).

Rate of decomposition=$((W-We)-wo)/wo/T$    (Formula 4)

In Formula 4, W represents the mass of the tube containing the sample, which was recorded after freeze-drying; and We represents the blank mass of the tube that was recorded in advance. wo represents the actual amount of addition of the sample. T represents the time taken for shaking in the collagenase solution.

The rate of decomposition of the biocompatible polymer film measured by the method described above is not particularly limited; however, the rate of decomposition is generally 0.1 to 20 [mass %/hour], preferably 0.5 to 20 [mass %/hour], more preferably 1 to 10 [mass %/hour], and particularly preferably 5 to 10 [mass %/hour].

(4) Method for Producing Cartilage Regenerative Material

The invention also provides a method for producing the cartilage regenerative material of the invention described above.

The production method includes Step A of freeze-drying an aqueous solution including a biocompatible polymer and obtaining a porous body; Step B of inoculating chondrocytes into the porous body obtained in Step A and culturing the chondrocytes; and Step C of providing a biocompatible polymer film.

Step A can be carried out as described in the above section "(1-4) Method for producing porous body of biocompatible polymer". In Step A, preferably, a porous body can be obtained by stirring an aqueous solution including a biocompatible polymer and then freeze-drying the aqueous solution.

Step B is a step of inoculating chondrocytes into the porous body and culturing the chondrocytes. The inoculation and culturing of chondrocytes in the porous body can be carried out by a conventional method.

By regulating the amount of use of chondrocytes with respect to the porous body and the duration of culture, the proportion of the region in which the cartilage matrix exists in a region extending from the surface of the transplant face of the porous body to a depth of 150 μm along the thickness (cartilage matrix filling proportion on the transplant face side) and the proportion of the region in which cartilage matrix exists in a region extending from the surface of the articular cavity face of the porous body to a depth of 150 μm along the thickness (cartilage matrix filling proportion on the articular cavity face side) can be regulated.

Step C is a step of providing a biocompatible polymer film. As described in the above section "(3) Biocompatible polymer film" in the present specification, a biocompatible polymer film can be provided.

(5) Method of Using Cartilage Regenerative Material

The cartilage regenerative material of the invention can be used for the purpose of cell transplantation to a diseased site of cartilage defect. Examples of the disease associated with cartilage defect include, but are not particularly limited to, arthrosis deformans, osteochondral defect, osteochondritis dissecans, traumatic cartilage injury, osteoarthritis, relapsing polychondritis, achondroplasia, injury of intervertebral discs, and hernia of intervertebral discs.

Examples of the method for transplantation include incision, injection, arthroscopy, and endoscopy. Regarding the cartilage regenerative material of the invention, unlike cell transplants such as a cell sheet, the size of the cartilage regenerative material can be made small, and therefore, a less invasive transplantation method such as transplantation by injection is enabled.

As described in section "[19] Evaluation of effectiveness of split transplantation of sponge with cartilage matrix (sufficient cartilage matrix filling proportion) in the Examples, it has been verified, concerning the cartilage regenerative material of the invention, that cartilage regeneration is recognized even in a case in which the cartilage regenerative material is subjected to split transplantation. Therefore, it is also possible to split a porous body including chondrocytes and cartilage matrix once and then transplant the split parts onto the site of defect.

Furthermore, as described in section "[20] Verification of whether fixation to site of defect is appropriate" in the Examples, the cartilage regenerative material of the invention is such that the cartilage regenerative material can be fixed to a site of defect with pins after transplantation. The material of the pins is not particularly limited; however, it is preferable to use a biocompatible polymer. Specific examples and preferred range of the biocompatible polymer that constitutes the pins are the same as those in the case of the biocompatible polymer that constitutes the porous body of a biocompatible polymer, and specifically, the specific examples and the preferred range are as described in the above sections (1-1) Biocompatible polymer, (1-2) Cross-linking, and (1-3) Recombinant gelatin in the present specification. The biocompatible polymer that constitutes the pins may be the same as, or may be different from, the biocompatible polymer that constitutes the porous body of a biocompatible polymer.

The amount used in the case of transplanting the cartilage regenerative material of the invention can be appropriately selected according to the diseased state or the like; however, the number of cells to be transplanted is preferably $1.0 \times 10^4$ cells/cm$^3$ to $2.0 \times 10^7$ cells/cm$^3$, and more preferably $2.5 \times 10^5$ cells/cm$^3$ to $5.0 \times 10^6$ cells/cm$^3$.

Regarding the number of times of transplantation of the cartilage regenerative material of the invention, transplantation may be carried out only once, or transplantation may be carried out two or more times as necessary.

(6) Applications and Cartilage Regeneration Method

According to the invention, there is provided a cartilage regenerative material intended for use for the treatment of cartilage regeneration, the cartilage regenerative material including a porous body of a biocompatible polymer and a biocompatible polymer film, in which the porous body contains chondrocytes and cartilage matrix, and the cartilage matrix exists in a region of 10% or more of a region extending from the surface of the transplant face of the porous body to a depth of 150 μm along the thickness. Preferred ranges of the various constituent components are similar to those described above in the present specification.

According to the invention, there is provided a cartilage regeneration method including a step of transplanting the cartilage regenerative material of the invention as described above, to a patient in need of cartilage regeneration. Preferred ranges of the various constituent components of the cartilage regenerative material are as described above in the present specification.

According to the invention, there is provided use of a porous body of a biocompatible polymer and a biocompatible polymer film for the production of a cartilage regenerative material, in which the porous body contains chondrocytes and cartilage matrix, and the cartilage matrix exists in a region of 10% or more of a region extending from the surface of the transplant face of the porous body to a depth of 150 μm along the thickness. Preferred ranges of the porous body of a biocompatible polymer and the biocompatible polymer film are as described above in the present specification.

The invention will be explained more specifically by way of the following Examples; however, the invention is not intended to be limited by the following Examples.

EXAMPLES

[1] Recombinant Peptide (Recombinant Gelatin)

As a recombinant peptide (recombinant gelatin), the following CBE3 was prepared (described in WO2008/10304 1A).

CBE3:
Molecular weight: 51.6 kD
Structure: GAP[(GXY)$_{63}$]$_3$G (SEQ ID NO: 11)
Number of amino acid residues: 571
RGD sequence: 12 sequences
Imino acid content: 33%
Almost 100% of the amino acid residues constitute a repeating structure of GXY. Serine, threonine, asparagine, tyrosine, and cysteine were not included in the amino acid sequence of CBE3. CBE3 comprises an ERGD sequence.
Isoelectric point: 9.34
GRAVY value: −0.682
1/IOB value: 0.323
Amino acid sequence (SEQ ID NO: 1 in the Sequence Listing) (Identical to SEQ ID NO:3 disclosed in WO2008/103041A. However, X at the end was corrected to "P")

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G

Furthermore, a porous body and a sponge according to the present specification are synonyms.

[2] Production of Recombinant Peptide Porous Body

[PTFE Thick Cylindrical Container]

A cylindrical cup-shaped container made of polytetrafluoroethylene (PTFE) and having a bottom face thickness of 3 mm, a diameter of 51 mm, a lateral face thickness of 8 mm, and a height of 25 mm was prepared. The cylindrical cup was such that when the curved face was erected as the lateral face, the lateral face was closed with a PTFE plate having a thickness of 8 mm, and the bottom face (circular-shaped flat plate) was also closed with a PTFE plate having a thickness of 3 mm. Meanwhile, the cylindrical cup had an open top face. Therefore, the inner diameter of the cylindrical cup was 43 mm. Hereinafter, this container will be referred to as PTFE thick cylindrical container.

[Aluminum Glass Plate Cylindrical Container]

A cylindrical cup-shaped container made of aluminum and having a thickness of 1 mm and a diameter of 47 mm was prepared. The cylindrical cup was such that when the curved face was erected as the lateral face, the lateral face was closed with an aluminum plate with a thickness of 1 mm, and the bottom face (circular-shaped flat plate) was also closed with an aluminum plate having a thickness of 1 mm. Meanwhile, the cylindrical cup had an open top face. A TEFLON (registered trademark) plate having a thickness of 1 mm was uniformly lined over the entire surface on the inner side of the lateral face, and as a result, the inner diameter of the cylindrical cup was 45 mm. The bottom face of this container was in a state of being joined with a glass plate having a thickness of 2.2 mm on the outside of aluminum. Hereinafter, this container will be referred to as an aluminum glass cylindrical container.

[Freezing Step with Small Temperature Difference, and Drying Step]

An aqueous solution of CBE3 was poured respectively into the PTFE thick cylindrical container and the aluminum glass plate cylindrical container, and the aqueous solution of CBE3 was cooled through the bottom face using a cooling shelf board inside a vacuum freeze-drying machine (TF5-85ATNNN: Takara Co., Ltd.).

The container, the final concentration of the aqueous solution of CBE3, the liquid amount, and the setting of the shelf board temperature employed in this case were as described below.

Condition A:
PTFE thick cylindrical container, final concentration of the aqueous solution of CBE3: 4 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased (1.9×10$^5$ Pa). Subsequently, the frozen product was removed from the vacuum freeze-drying machine. Thus, a porous body was obtained.

Condition B:
Aluminum glass plate cylindrical container, final concentration of aqueous solution of CBE3: 4 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased (1.9×10$^5$ Pa). Subsequently, the frozen product was removed from the vacuum freeze-drying machine. Thus, a porous body was obtained.

Condition C:
PTFE thick cylindrical container, final concentration of the aqueous solution of CBE3: 4 mass %, amount of the aqueous solution: 10 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased ($1.9 \times 10^5$ Pa). Subsequently, the frozen product was removed from the vacuum freeze-drying machine. Thus, a porous body was obtained.

[3] Measurement of Temperature Difference in Various Freezing Steps

In regard to each of Condition A to Condition C, the liquid temperature of the liquid surface at the circle center in the container was measured as the liquid temperature at the remotest place from the cooling side (non-cooling surface liquid temperature) within the solution, and the liquid temperature at the bottom in the container was measured as the liquid temperature closest to the cooling side (cooling surface liquid temperature) within the solution.

Figure 2:
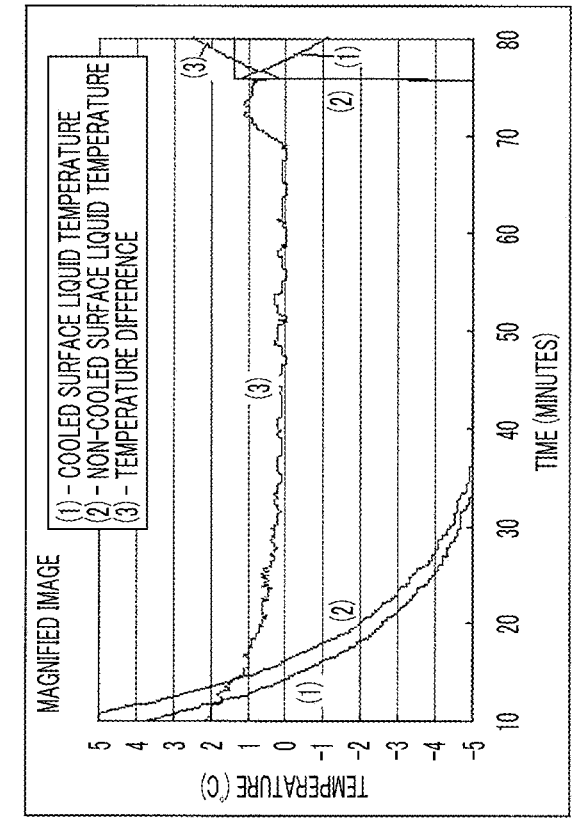
FIG. 2 illustrates a liquid temperature profile obtained under Condition B.
Figure 2:
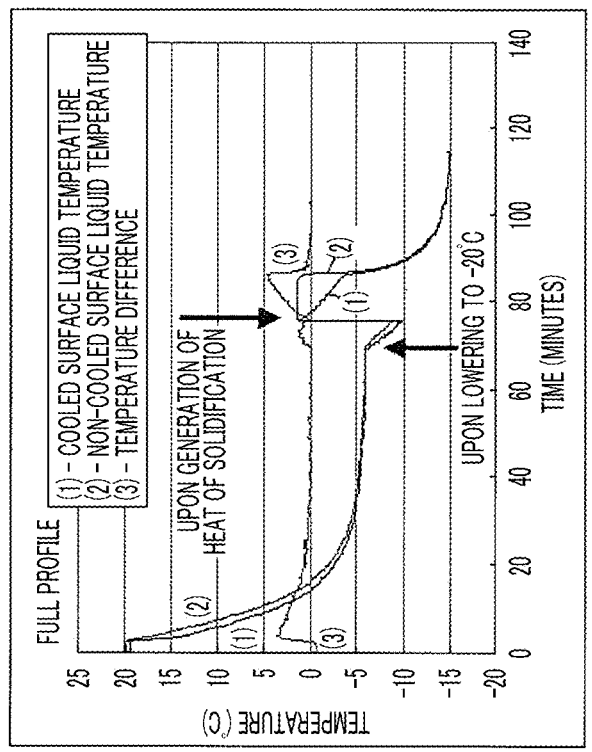
Figure 3:
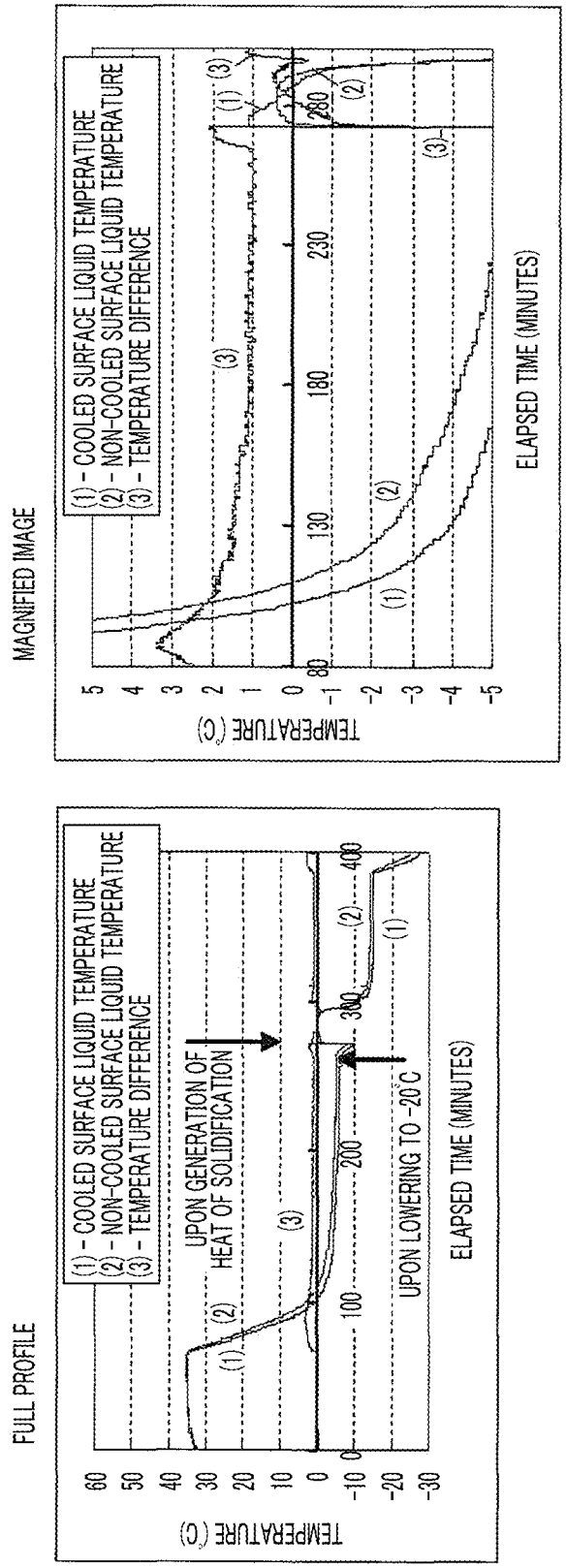
FIG. 3 illustrates a liquid temperature profile obtained under Condition C.

As a result, the profiles of the respective temperatures and the temperature differences were obtained as shown in FIG. 1 to FIG. 3.

From these FIG. 1, FIG. 2, and FIG. 3, it can be seen that under Condition A, Condition B, and Condition C, the liquid temperature was below the melting point, 0° C., in the section with the shelf board temperature set at −10° C. (before lowering to −20° C.), and that state was a state in which freezing had not occurred (unfrozen/overcooled). In this state, the temperature difference between the cooling surface liquid temperature and the non-cooling surface liquid temperature was 2.5° C. or less. Subsequently, as the shelf board temperature was further lowered to −20° C., a time point at which the liquid temperature rapidly increased to near 0° C. was confirmed. Thus, it is understood that the heat of solidification was generated here, and freezing was initiated. It could also be confirmed that ice formation had actually started at that time point. Subsequently, a certain time elapsed while the temperature remained at near 0° C. Here, a state in which water and ice existed as a mixture was maintained. Lastly, temperature drop started again from 0° C.; however, at this time, the liquid portion had disappeared, and only ice was left. Therefore, the temperature that was measured was the solid temperature inside the ice, and this was not a liquid temperature.

In the following description, the temperature difference at the time when the non-cooling surface liquid temperature reached the melting point (0° C.), the temperature difference immediately before lowering of the shelf board temperature from −10° C. to −20° C., and the temperature difference immediately before the generation of the heat of solidification will be described in conjunction with Condition A, Condition B, and Condition C. The "temperature difference immediately before" as used in the present specification means the largest temperature difference among the temperature differences detectable in a period between 1 second and 20 seconds before the main event.

Condition A

Temperature difference at the time when the liquid temperature of the non-cooling surface reached the melting point (0° C.): 1.1° C.

Temperature difference immediately before lowering from −10° C. to −20° C.: 0.2° C.

Temperature difference immediately before the generation of the heat of solidification: 1.1° C.

Condition B

Temperature difference at the time when the liquid temperature of the non-cooling surface reached the melting point (0° C.): 1.0° C.

Temperature difference immediately before lowering from −10° C. to −20° C.: 0.1° C.

Temperature difference immediately before the generation of the heat of solidification: 0.9° C.

Condition C

Temperature difference at the time when the liquid temperature of the non-cooling surface reached the melting point (0° C.): 1.8° C.

Temperature difference immediately before lowering from −10° C. to −20° C.: 1.1° C.

Temperature difference immediately before the generation of the heat of solidification: 2.1° C.

Hereinafter, these will be referred to as "freezing step with small temperature difference/porous body".

[4] Freezing Step with Small Temperature Difference in 1 Mass % Ethanol-Containing Solution, and Drying Step A 1 mass % (w/w) ethanol-containing aqueous solution of CBE3 was respectively poured into the PTFE thick cylindrical container and the aluminum glass plate cylindrical container, and the aqueous solution of CBE3 was cooled through the bottom face using a cooling shelf board inside a vacuum freeze-drying machine (TF5-85ATNNN: Takara Co., Ltd.). Since an ethanol-containing aqueous solution at a final concentration of 1 mass % was used, the melting point was −0.4° C. The melting point change at the ethanol/water concentration ratio was calculated from literature "Pickering S. U.: A Study of the Properties of Some Strong Solutions. J. Chem. Soc. London, 63 (1893), 998-1027".

The container, the final concentration of the aqueous solution of CBE3, the liquid amount, and the setting of the shelf board temperature employed in this case were as described below.

Condition AA:

PTFE thick cylindrical container, final concentration of the aqueous solution of CBE3: 4 mass %, final ethanol concentration: 1 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased. Subsequently, the frozen product was removed from the vacuum freeze-drying machine. Thus, a porous body was obtained.

Condition BB:

Aluminum glass plate cylindrical container, final concentration of the aqueous solution of CBE3: 4 mass %, final ethanol concentration: 1 mass %, amount of the aqueous solution: 4 mL. Regarding the setting of the shelf board temperature, cooling was performed until the temperature reached −10° C., and freezing was performed for 1 hour at −10° C., subsequently for 2 hours at −20° C., for 3 hours at −40° C., and lastly for 1 hour at −50° C. Subsequently, the shelf board temperature was returned to the setting of −20° C., and then the present frozen product was subjected to vacuum drying for 24 hours at −20° C. After 24 hours, while vacuum drying was still continued, the shelf board temperature was raised to 20° C., and vacuum drying was performed for another 48 hours at 20° C. until the degree of vacuum sufficiently decreased. Subsequently, the frozen product was removed from the vacuum freeze-drying machine. Thus, a porous body was obtained.

[Measurement of Temperature Difference of 1 Mass % Ethanol-Containing Solution in Freezing Step]

In regard to Condition AA and Condition BB, the liquid temperature of the liquid surface at the circle center in the container was measured as the liquid temperature at the remotest place from the cooling side (non-cooling surface liquid temperature) within the solution, and the liquid temperature at the bottom in the container was measured as the liquid temperature closest to the cooling side (cooling surface liquid temperature) within the solution. Here, since 1 mass % ethanol was used as the solvent, the solvent melting point was −0.4° C. The melting point change at the ethanol/water concentration ratio was calculated from literature "Pickering S. U.: A Study of the Properties of Some Strong Solutions. J. Chem. Soc. London, 63 (1893), 998-1027".

Figure 4:
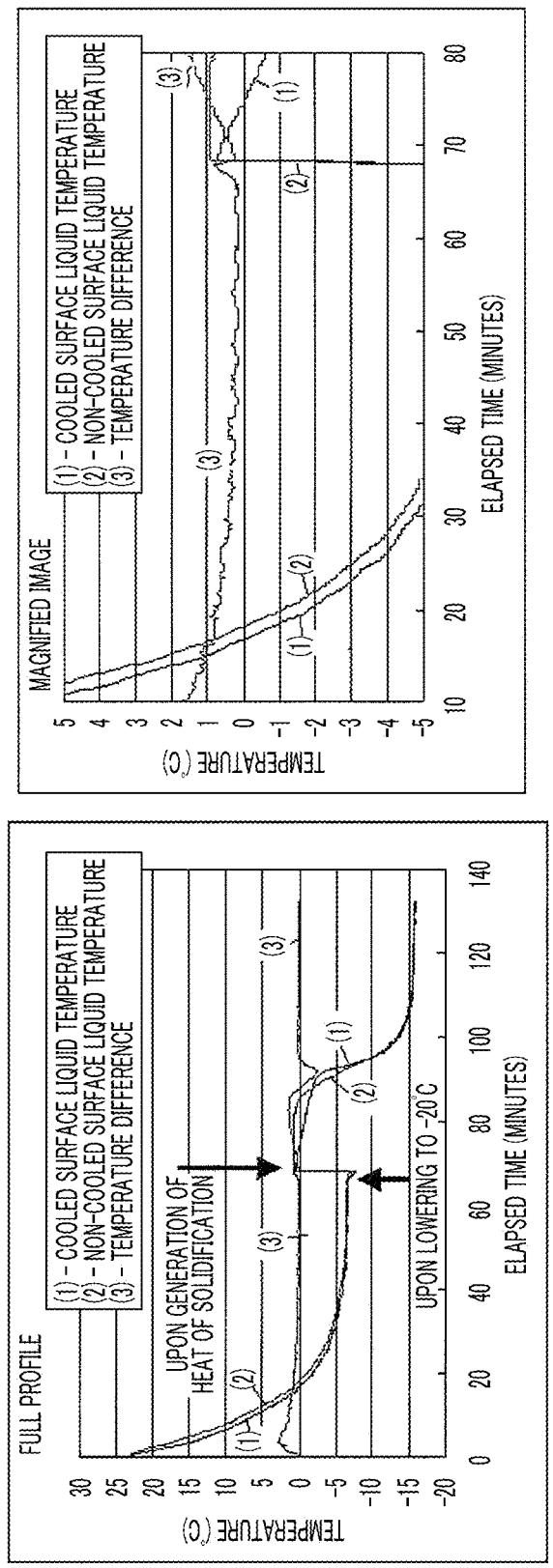
FIG. 4 illustrates a liquid temperature profile obtained under Condition AA.
Figure 5:
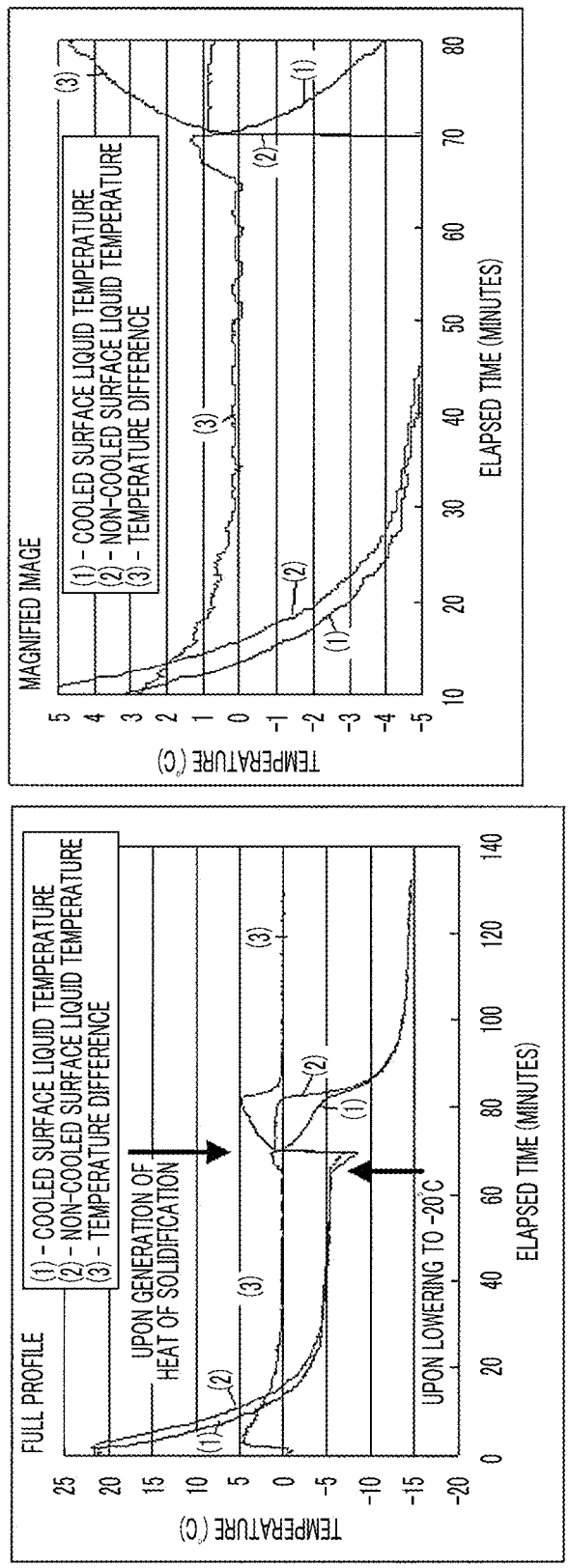
FIG. 5 illustrates a liquid temperature profile obtained under Condition BB.
Figure 6:
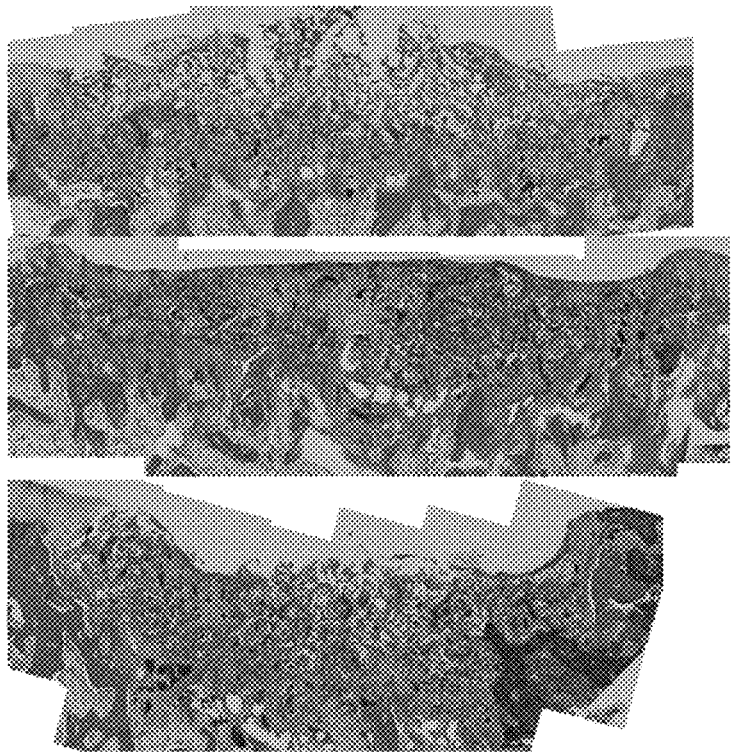
FIG. 6 shows the results of staining of a tissue onto which only a sponge was transplanted (without film).
Figure 7:
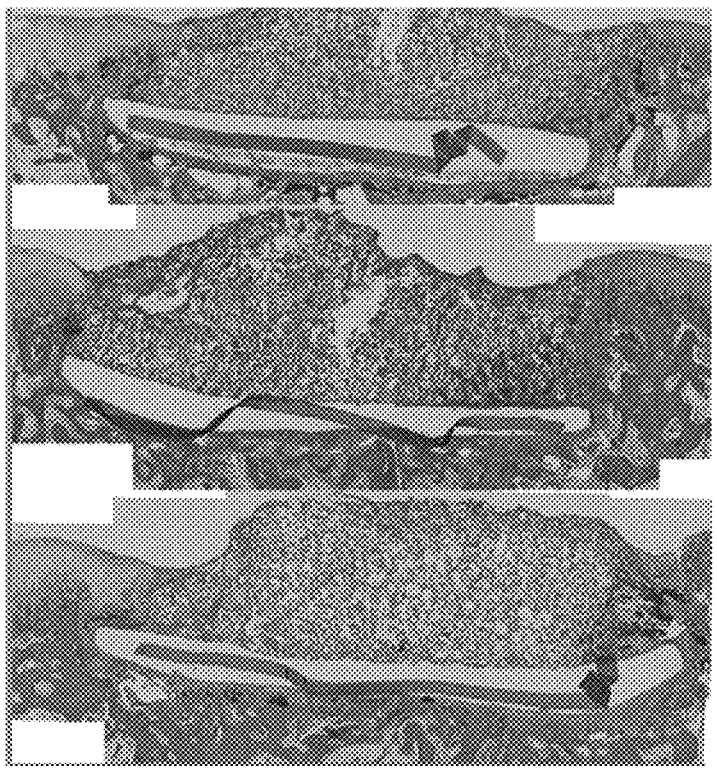
FIG. 7 shows the results of staining of a tissue onto which a sponge (without cells) and a film were transplanted.

As a result, the profiles of the respective temperatures and the temperature differences were obtained as shown in FIG. 4 to FIG. 5. From these FIG. 4 and FIG. 5, it can be seen that under Condition AA and Condition BB, the liquid temperature was below the melting point, −0.4° C., in the section with the shelf board temperature set at −10° C., and that state was a state in which freezing had not occurred (unfrozen/overcooled). In this state, the temperature difference between the cooling surface liquid temperature and the non-cooling surface liquid temperature was 2° C. or less. Subsequently, as the shelf board temperature was further lowered to −20° C., a time point at which the liquid temperature rapidly increased to near −0.4° C. was confirmed. Thus, it is understood that the heat of solidification was generated here, and freezing was initiated. It could also be confirmed that ice formation had actually started at that time point. Subsequently, a certain time elapsed while the temperature remained at near −0.4° C. Here, a state in which water and ice existed as a mixture was maintained. Lastly, temperature drop started again from 0° C.; however, at this time, the liquid portion had disappeared, and only ice was left. Therefore, the temperature that was measured was the solid temperature inside the ice, and this was not a liquid temperature.

In the following description, the temperature difference at the time when the non-cooling surface liquid temperature reached the melting point (−0.4° C.), the temperature difference immediately before lowering of the shelf board temperature from −10° C. to −20° C., and the temperature difference immediately before the generation of the heat of solidification will be described in conjunction with Condition AA and Condition BB.

Condition AA

Temperature difference at the time when the liquid temperature of the non-cooling surface reached the melting point (−0.4° C.): 0.8° C.

Temperature difference immediately before lowering from −10° C. to −20° C.: 0.3° C.

Temperature difference immediately before the generation of the heat of solidification: 0.8° C.

Condition BB

Temperature difference at the time when the liquid temperature of the non-cooling surface reached the melting point (−0.4° C.): 1.3° C.

Temperature difference immediately before lowering from −10° C. to −20° C.: 0.0° C.

Temperature difference immediately before the generation of the heat of solidification: 1.3° C.

As a result, it was found that even under Condition AA and Condition BB, the porous body can be produced as "freezing step with small temperature difference/porous body", similarly to Condition A and Condition B.

[5] Production of Recombinant Peptide Tin Layer Frozen Porous Body

A cylindrical cup-shaped container made of aluminum and having a thickness of 1 mm and a diameter of 47 mm was prepared. The cylindrical cup was such that when the curved face was erected as the lateral face, the lateral face was closed with an aluminum plate having a thickness of 1 mm, and the bottom face (circular-shaped flat plate) was also closed with an aluminum plate having a thickness of 1 mm. Meanwhile, the cylindrical cup had an open top face. A TEFLON (registered trademark) plate having a thickness of 1 mm was uniformly lined over the entire surface on the inner side of the lateral face, and as a result, the inner diameter of the cylindrical cup was 45 mm. Hereinafter, this container will be referred to as cylindrical container.

An aqueous solution of CBE3 was prepared, and this aqueous solution of CBE3 was caused to flow into the cylindrical container. The aqueous solution of CBE3 was cooled through the bottom face using a cooling shelf board inside a refrigerator. In this case, the temperature of the cooling shelf board, the thickness of the heat-insulating plate (glass plate) interposed between the shelf board and the cylindrical container, the final concentration of the aqueous solution of CBE3 to be introduced, and the amount of the aqueous solution were as described below. Temperature of shelf board: −40° C., thickness of glass plate: 2.2 mm, final concentration of aqueous solution of CBE3: 4.0%, amount of aqueous solution: 4 mL. The frozen CBE3 block obtained as described above was freeze-dried, and a CBE3 porous body was obtained. The porous body obtained as described above will be hereinafter referred to as thin layer frozen porous body.

[6] Production of Recombinant Peptide Porous Body by Stirring

A stirring method porous body was produced using the recombinant peptide CBE3. In the present Example, a solution was prepared at the following composition, and the solution was stirred for 30 seconds at 17,000 rpm with a homogenizer (AM-11, manufactured by Nihon Seiki Co., Ltd.) at 4° C. The solution was transferred into an aluminum cup container and was rapidly cooled for 3 hours at −80° C. Subsequently, freeze-drying was performed for 3 days in a freeze-dryer, and thus a porous body was obtained. The porous body obtained as described above will be hereinafter referred to as stirring method porous body.

Composition: 10-mL portion of 10 mass % of porous body (CBE3: 1,000 mg, ultrapure water: 9,895 μL, 1 mol/L HCl: 105 μL)

[7] Crosslinking of Recombinant Peptide Porous Body

For the freezing step with small temperature difference/porous body obtained in the above section [2] and [3], the ethanol-containing freezing step with small temperature difference/porous body obtained in the above section [4], the thin layer frozen porous body obtained in the above section [5], and the stirring method porous body obtained in the above section [6], the respective porous bodies were subjected to thermal crosslinking for 20 hours at 160° C. under reduced pressure.

[8] Evaluation of Pore Size of Recombinant Peptide Porous Body

The various porous bodies obtained in the above section [7] were swollen with physiological saline for a sufficient time. Subsequently, frozen tissue slices were produced with a microtome, and HE (haematoxylin and eosin) stained specimens were produced. Cross-sectional images having a size of 1.5 mm on the actual scale were prepared from the specimens, and the individual pore areas were measured. Subsequently, the equivalent circle diameter obtainable in a case in which the area was considered equivalent to a circle was calculated, and this value was designated as the pore size. The average value of 20 or more sites of these pores was designated as the average pore size. As a result, the average pore size of the freezing step with small temperature difference/porous body derived from sections [2] and [3] was 59 μm, the average pore size of the ethanol-containing freezing step with small temperature difference/porous body derived from section [4] was 72 μm, the average pore size of the stirring method porous body derived from section [6] was 82 μm, and the average pore size of the thin layer frozen porous body derived from section [5] was 45 μm.

[9] Method for Producing Recombinant Peptide Film

An aqueous solution of CBE3 at a concentration of 4 mass % was prepared, and 5.4 ml of this aqueous solution of CBE3 was caused to flow into a plastic tray provided with a silicon frame (8 cm×3.5 cm). This plastic tray was transferred into a refrigerator, and the aqueous solution was dried until no moisture left. Thus, a recombinant peptide film was obtained. The recombinant peptide film was taken out from the plastic tray/silicon frame, and was subjected to thermal crosslinking at 160° C. under reduced pressure (crosslinking time was 48 hours or 72 hours). Thus, a sample for an animal test was obtained.

[10] Method for Measuring Degree of Crosslinking

The degree of crosslinking (number of crosslinks per molecule) of the film produced in the above section [9] was calculated. For the measurement, a TNBS (2,4,6-trinitrobenzenesulfonic acid) method was used.

<Preparation of Sample>

A sample (about 10 mg), a 4 mass % aqueous solution of $NaHCO_3$ (1 mL), and a 1 mass % aqueous solution of TNBS (2 mL) were introduced into a glass vial, and the mixture was shaken for 3 hours at 37° C. Subsequently, 37 mass % hydrochloric acid (10 mL) and pure water (5 mL) were added thereto, and then the mixture was left to stand for 16 hours or longer at 37° C. The resultant was used as a sample.

<Preparation of Blank>

A sample (about 10 mg), a 4 mass % aqueous solution of $NaHCO_3$ (1 mL), and a 1 mass % aqueous solution of TNBS (2 mL) were introduced into a glass vial, 37 mass % hydrochloric acid (3 mL) was added thereto immediately thereafter, and the mixture was shaken for 3 hours at 37° C. Subsequently, 37 mass % hydrochloric acid (7 mL) and pure water (5 mL) were added thereto, and then the mixture was left to stand for 16 hours or longer at 37° C. The resultant was used as a blank.

The light absorbance (345 nm) of a dilution of the sample obtained by diluting 10 times with pure water, and the light absorbance of the blank were measured, and the degree of crosslinking (number of crosslinks per molecule) was calculated from (Formula 2) and (Formula 3).

$$(As-Ab)/14600 \times V/w \quad \text{(Formula 2)}$$

(Formula 2) represents the amount of lysine (molar equivalent) per gram of the recombinant peptide.

In Formula 2, As represents the light absorbance of the sample; Ab represents the light absorbance of the blank; V represents the amount of the reaction liquid (g); and w represents the mass (mg) of the recombinant peptide.

$$1-(\text{Sample (Formula 1)/uncrosslinked recombinant peptide (Formula 1)}) \times 34 \quad \text{(Formula 3)}$$

(Formula 3) represents the number of crosslinks per molecule.

As a result, the film obtained by crosslinking for 48 hours in the above section [9] had a degree of crosslinking of 6, and the film obtained by crosslinking for 72 hours in the above section [6] had a degree of crosslinking of 13. The degree of crosslinking of the porous body of the above section [7] measured in the same manner was 9.

[11] Method for Measuring Rate of Decomposition

The rate of decomposition of the film produced in the above section [9] was evaluated.

5 mg of a sample produced in the above section [9] was introduced into a plastic tube, the mass of which had been measured in advance, and the actual amount of addition was recorded.

2.5 mg of Actinomyces-derived collagenase was dissolved in 50 ml of phosphate buffered saline (PBS), and a collagenase solution was obtained. 1 ml of this collagenase solution was added to the tube containing the sample, and the content was mixed by vortexing. Subsequently, the mixture was shaken for 5 hours at 37° C. Subsequently, the tube was centrifuged for 1 minute at 10,000 G, and the supernatant was removed using a pipette. 1 ml of ultrapure water was added to the tube, and the content was mixed by vortexing. Subsequently, the tube was centrifuged for 1 minute at 10,000 G, and the supernatant was removed using a pipette. This operation was repeated one more time. Subsequently, the sample was freeze-dried, and the mass of the tube containing the sample was recorded.

The rate of decomposition of the film was calculated from the following formula (Formula 4).

$$\text{Rate of decomposition}=((W-We)-wo)/wo/T \quad \text{(Formula 4)}$$

In Formula 4, W represents the mass of the tube containing the sample, which was recorded after freeze-drying; and We represents the blank mass of the tube that was recorded in advance. wo represents the actual amount of addition of the sample. T represents the time taken for shaking in the collagenase solution, and in this test, T was 5 hours.

As a result, the film of the above section [9] resulted in a rate of decomposition of 6.9 [mass %/hour] under crosslinking for 48 hours, and a rate of decomposition of 0.5 [mass %/hour] under crosslinking for 72 hours.

[12] Method for Collecting Rabbit Chondrocytes 3- to 4-week old Japanese white rabbits were victimized by intravenous administration of somnopentyl, and cartilage tissues were collected from femurs and tibias (humeri). The cartilage tissues were disinfected with an isodine dilution and were washed with DULBECCO's phosphate buffered saline (DPBS). 0.25 mass % trypsin was added thereto, and the mixture was allowed to react for about 1 hour at 37° C. Subsequently, the mixture was allowed to react with a 3,000 units/mL collagenase type IX solution for about 3 hours, the digest was passed through a cell strainer, and the residue was eliminated. Subsequently, a medium was added to the cells, and the mixture was centrifuged in order to eliminate the collagenase. The supernatant was removed, and a medium was added to the residue. Rabbit chondrocytes were obtained through this process.

The medium used as described above was a medium for chondrocyte culture in all cases, and the medium is a medium composed of DULBECCO's modified Eagle medium (DMEM), 10 vol % fetal bovine serum (FBS), 20 mM HEPES (4-(2-hydroyethyl)-1-piperazine ethanesulfonic acid), 50 μg/mL magnesium L-ascorbyl phosphate, 0.25 μg/mL amphotericin B, and 50 μg/mL gentamycin. In the following description, in a case in which the description "medium" is given, this medium was used in all the cases.

[13] Production of Rabbit Chondrocyte Culture Sponges Having Different Cartilage Matrix Filling Proportions The stirring method porous body (pore size 82 μm) prepared in the above section [6] was cut out into a size with a diameter of 5 mm and a thickness of 2 mm, the rabbit chondrocytes prepared in the above section [12] were inoculated thereon at a concentration of $5.0 \times 10^6$ cells/cm$^3$, and culture was carried out. Therefore, a sponge with cartilage matrix was obtained. Here, a porous body that was not inoculated with rabbit chondrocytes was also prepared, and that was prepared as a sponge without cartilage matrix. Even in the case of using the ethanol-containing freezing step with small temperature difference/porous body (pore size 72 μm) prepared in the above sections [7] and [8], the same results were obtained as the subsequent results. Therefore, in the following description, the data of the stirring method porous body derived from [6] will be suggested as a representative example.

Figure 8:
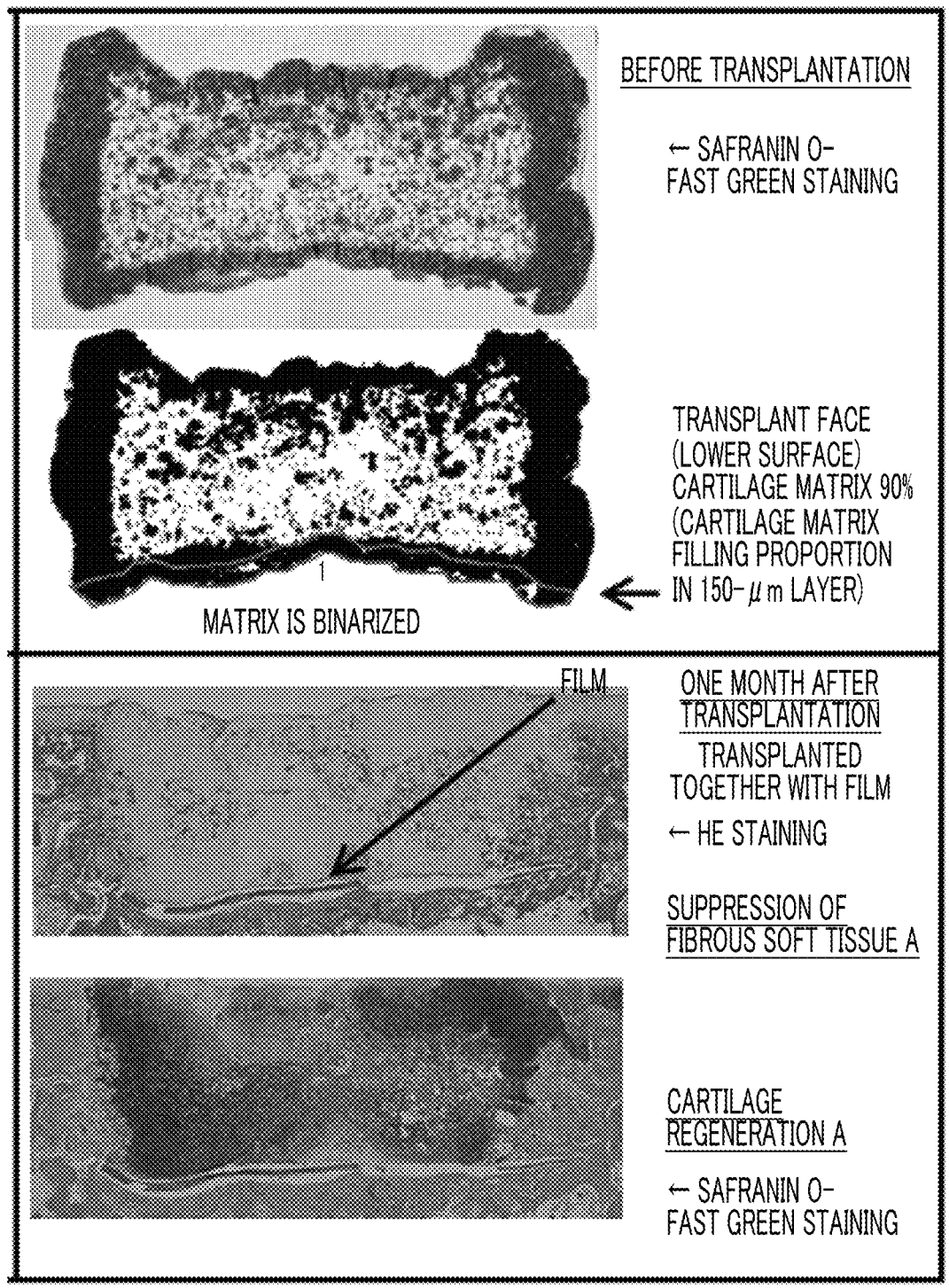
FIG. 8 shows the results of staining of a tissue before transplantation and after transplantation of a cell culture sponge having a cartilage matrix filling proportion at the transplant face of 90% and a film.
Figure 9:
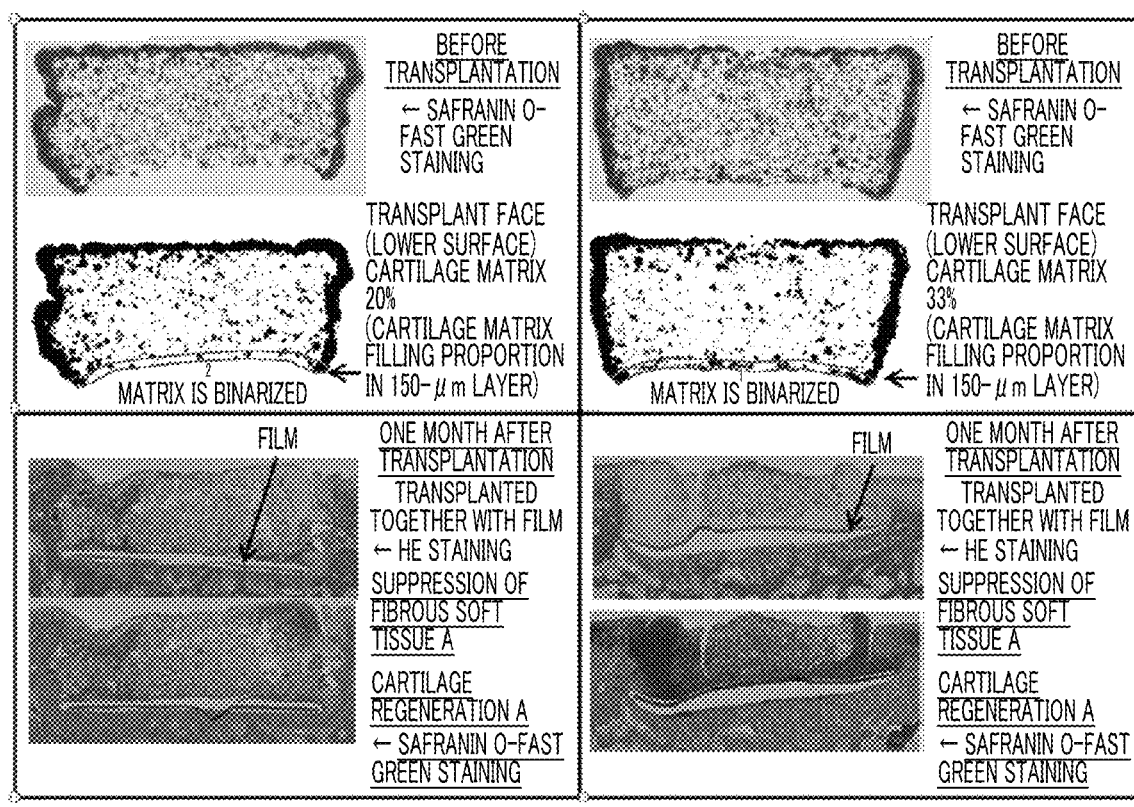
FIG. 9 shows the results of staining of a tissue before transplantation and after transplantation of a cell culture sponge having a cartilage matrix filling proportion at the transplant face of 20% or 33% and a film.
Figure 10:
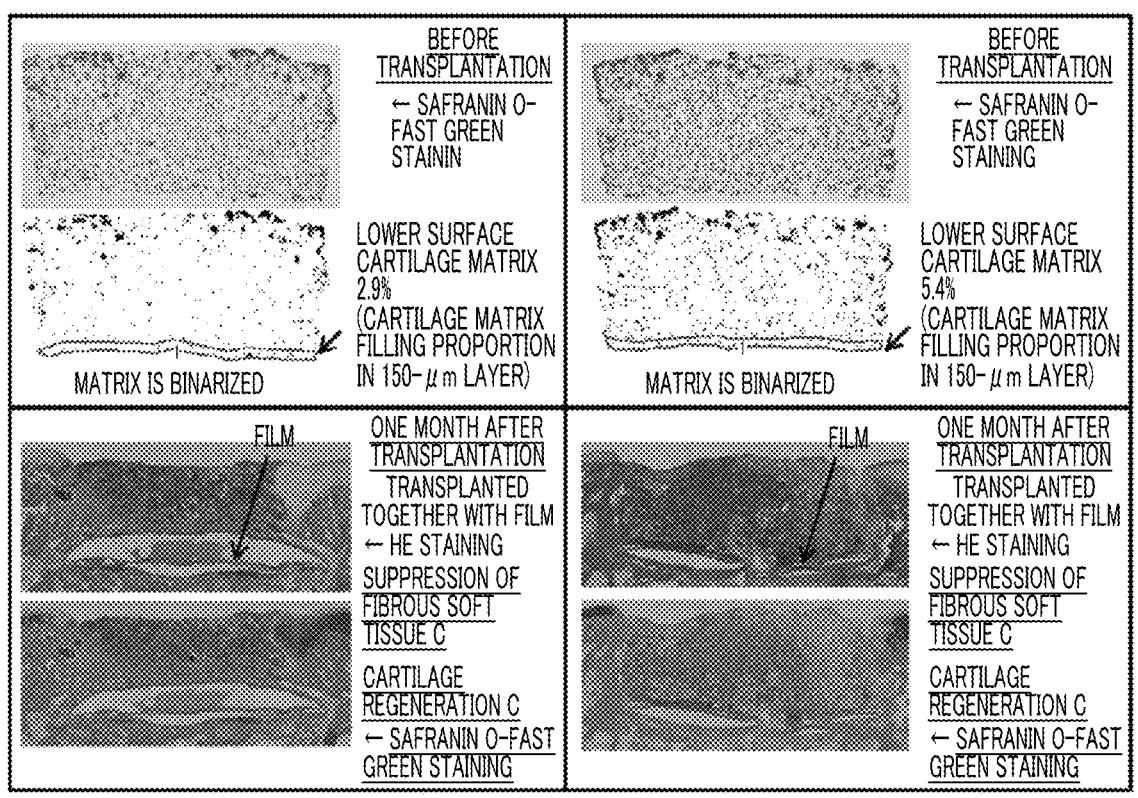
FIG. 10 shows the results of staining of a tissue before transplantation and after transplantation of a cell culture sponge having a cartilage matrix filling proportion at the transplant face of 2.9% or 5.4% and a film.
Figure 11:
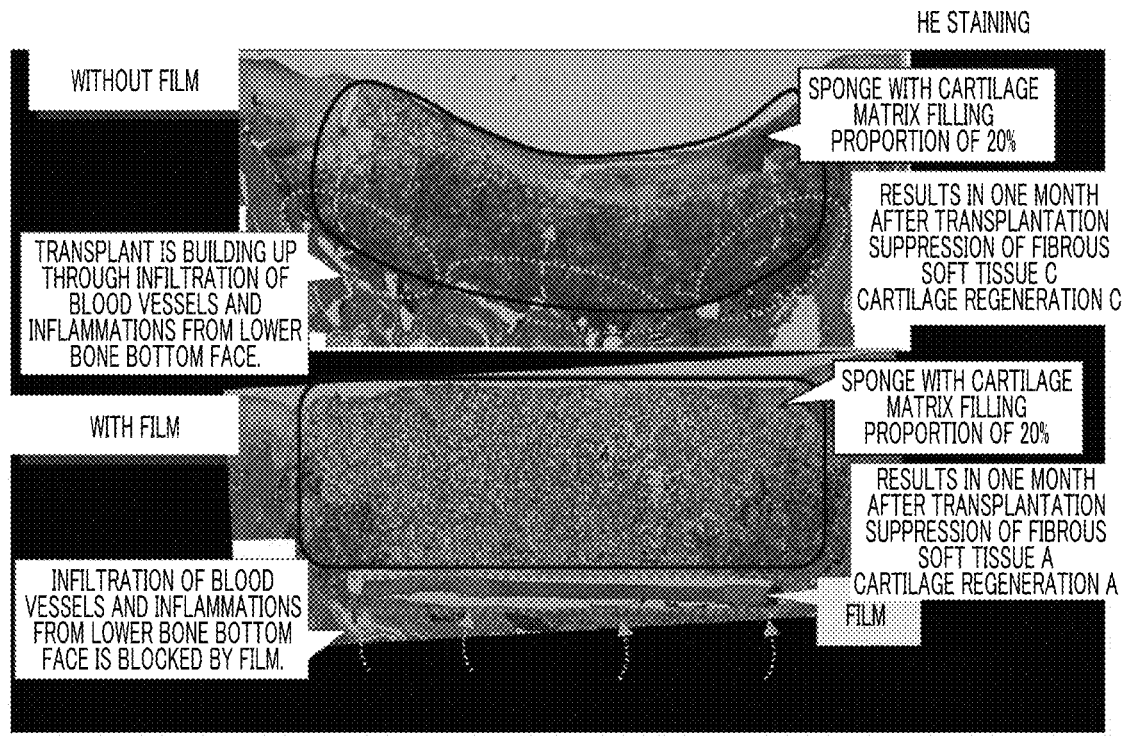
FIG. 11 shows the results of haematoxylin and eosin (HE) staining of a tissue onto which a cell culture sponge having a cartilage matrix filling proportion at the transplant face of 20% was transplanted without a film or with a film.
Figure 12:
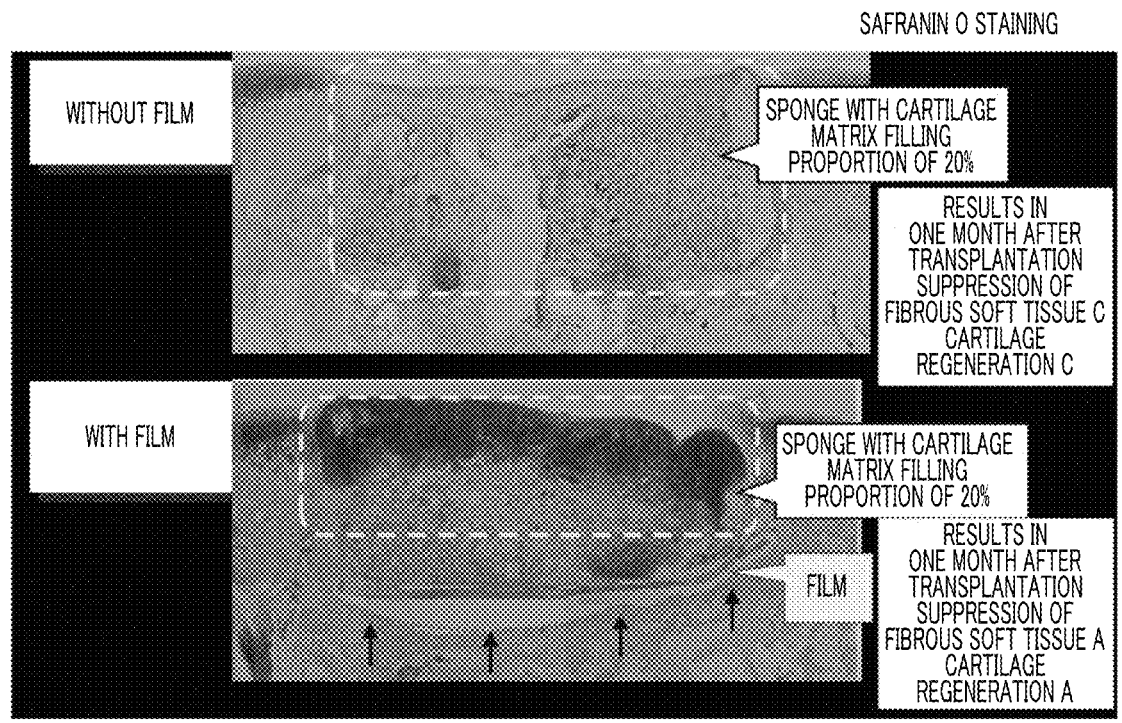
FIG. 12 shows the results of safranin O staining of a tissue onto which a cell culture sponge having a cartilage matrix filling proportion at the transplant face of 20% was transplanted without a film or with a film.

[14] Evaluation of Samples Having Different Cartilage Matrix Filling Proportions of Bottom Faces The sponge with cartilage matrix obtained by inoculating cells and culturing in the above section [13] could be used to produce sponges with cartilage matrix having different cartilage matrix filling proportions of the bottom faces with the elapse time of culture (3 days, 7 days, 14 days, 21 days, and 28 days). For the measurement of the cartilage matrix filling proportion of the bottom face, tissue slices of the sponge with cartilage matrix were produced (formalin fixation and paraffin embedment), and the cross-sections of the slices were visualized by performing safranin O staining. Thus, the cross-sections were evaluated (FIG. 8 to FIG. 10).

Particularly, attention was paid to the region having a thickness of 150 μm of the bottom face part of the stained tissue slices produced as such, and in this region having a thickness of 150 μm, cartilage matrix existed. Therefore, the area of the region in which safranin O staining produced positive results was measured. Meanwhile, the proportion of the area of the safranin O staining-positive region with respect to the total area of the region having a thickness of 150 μm was determined, and the proportion was designated as "cartilage matrix filling proportion in 150-μm layer". As a result, regarding the sponges with cartilage matrix produced in the above section [13], the "cartilage matrix filling proportions in 150-μm layer" were 2.9%, 5.4%, 20%, 33%, and 90%.

In all of the sponges having "cartilage matrix filling proportions in 150-μm layer" of 2.9%, 5.4%, 20%, 33%, and 90%, which were produced in the above sections [13] and [14], cartilage matrix existed in a region of 30% or more of a region extending from the surface of the articular cavity face to a depth of 150 μm along the thickness.

[15] Production of Rabbit Cartilage Defect Model

At a knee joint site of a 22-week old male Japanese white rabbit (Kitayama Labes Co., Ltd., SPF), an osteochondral defect having a size with a diameter of 5 mm and a depth of about 2 mm was produced.

[16] Evaluation of Sample Transplantation Onto Rabbit Cartilage Defect Model (One Month) (Influence of Cartilage Matrix Filling Proportion)

Samples of various evaluation objects were transplanted onto the rabbit cartilage defect sites produced in the above section [15], and the rabbits were autopsied at a time point of one month after the transplantation. Thus, osteochondral tissue slices of the periphery of the transplantation sites were produced. The tissues were subjected to formalin fixation and paraffin embedment, and thus tissue slices including the transplants were produced. Regarding staining of the slices, HE staining (haematoxylin and eosin staining), or safranin O staining, or safranin O and fast green staining were carried out.

Here, regarding the film in the case of using a film, samples obtained by cutting the films prepared in the above section [9] (since the same results were obtained for the films having a degree of crosslinking of 6 and the films having a degree of crosslinking of 13, no distinction was made between them in this Example) into the size of the low bottom face area (diameter: 5 mm) of the defect, were used. Furthermore, in the case of using a film, the film was transplanted in a state in which the film came to the transplant face (lower bone side). The positional relation of the sponge and the film in the case of transplanting the sponge and the film onto the rabbit osteochondral defect site is depicted in FIG. 19.

The samples evaluated and the results are presented in FIG. 6 to FIG. 12. Furthermore, cartilage regeneration and suppression of the infiltration of fibrous soft tissue were evaluated according to the following criteria. The results of the evaluation are summarized in Table 1.

Cartilage Regeneration

A: Satisfactory cartilage regeneration is recognized.

B: Slight cartilage regeneration is recognized in some part.

C: Cartilage regeneration is not recognized.

Suppression of Infiltration of Fibrous Soft Tissue

A: Suppression of the infiltration of fibrous soft tissue is recognized.

B: Suppression of the infiltration of fibrous soft tissue is slightly recognized.

C: Suppression of the infiltration of fibrous soft tissue is not recognized.

D: Infiltration of inflammation cannot be suppressed, and suppression of the infiltration of fibrous soft tissue is poorly achieved.

TABLE 1

| | Remarks for group | Summary of evaluation | Cartilage regeneration | Suppression of infiltration of fibrous soft tissue |
|---|---|---|---|---|
| Comparative Example 1 | Only sponge without cartilage matrix was transplanted. | Infiltration of inflammation cannot be suppressed, and suppression of infiltration of fibrous soft tissue is poor. Cartilage regeneration was not recognized. | C | D |
| Comparative Example 2 | Sponge without cartilage matrix was transplanted integrally with film having diameter of 5 mm, with the film being placed below the sponge. | Suppression of infiltration of inflammation was successful compared to the case of Comparative Example 1, and suppression of the infiltration of fibrous soft tissue was slightly recognized. Cartilage regeneration was not recognized. | C | B |

TABLE 1-continued

| | Remarks for group | Summary of evaluation | Cartilage regeneration | Suppression of infiltration of fibrous soft tissue |
|---|---|---|---|---|
| Comparative Example 3 | Sponge with cartilage matrix (cartilage matrix filling proportion: 2.9%) was transplanted integrally with film having diameter of 5 mm, with the film being placed below the sponge. | Suppression of infiltration of fibrous soft tissue was not recognized, and cartilage regeneration was also not recognized. | C | C |
| Comparative Example 4 | Sponge with cartilage matrix (cartilage matrix filling proportion: 5.4%) was transplanted integrally with film having diameter of 5 mm, with the film being placed below the sponge. | Suppression of infiltration of fibrous soft tissue was not recognized, and cartilage regeneration was also not recognized. | C | C |
| Example 1 | Sponge with cartilage matrix (cartilage matrix filling proportion: 20%) was transplanted integrally with film having diameter of 5 mm, with the film being placed below the sponge. | Suppression of infiltration of fibrous soft tissue was significantly recognized, and it was understood that cartilage regeneration was also satisfactory. | A | A |
| Example 2 | Sponge with cartilage matrix (cartilage matrix filling proportion: 33%) was transplanted integrally with film having diameter of 5 mm, with the film being placed below the sponge. | Suppression of infiltration of fibrous soft tissue was significantly recognized, and it was understood that cartilage regeneration was also satisfactory. | A | A |
| Example 3 | Sponge with cartilage matrix (cartilage matrix filling proportion: 90%) was transplanted integrally with film having diameter of 5 mm, with the film being placed below the sponge. | Suppression of infiltration of fibrous soft tissue was significantly recognized, and it was understood that cartilage regeneration was also satisfactory. | A | A |
| Comparative Example 5 | Only sponge with cartilage matrix (cartilage matrix filling proportion: 20%) was transplanted. | Suppression of infiltration of fibrous soft tissue was not recognized, and cartilage regeneration was also not recognized. | C | C |

From the results described above, it was found that in a case in which the "cartilage matrix filling proportion in 150-μm layer" was sufficient (20%, 33%, and 90%), and in a case in which the film was provided at the bottom face (transplant face), satisfactory suppression of the infiltration of fibrous soft tissue and satisfactory cartilage regeneration were brought about.

[17] Evaluation of Sample Transplantation Into Rabbit Cartilage Defect Model (Long-Term 6 Months) (Influence of Degree of Film Crosslinking)

Similarly to the method of the above section [16], sponges with cartilage matrix having the same cartilage matrix filling proportions (33%) (sections [13] and [14]), and films having different degrees of crosslinking (degrees of crosslinking of sections [9] and [10]: 6 and 13) were transplanted onto rabbit cartilage defect sites produced in the above section [15]. These were transplanted such that the film would exist at the transplant face (lower bone side). The rabbits were autopsied at a time point of 6 months after transplantation, and osteochondral tissue slices of the periphery of the sites of transplantation were produced. The tissue was subjected to formalin fixation, followed by paraffin embedment, and thus tissue slices including the transplant were produced. Regarding the slice staining, HE staining (haematoxylin and eosin staining), or safranin O staining, or safranin O and fast green staining were carried out.

Here, regarding the film in the case of using a film, samples obtained by cutting the films prepared in the above section [9], which had two degrees of crosslinking (measured in section [10]) (degree of crosslinking: 6 and 13), respectively into the size of the low bottom face area (diameter: 5 mm) of the defect, were used.

Figure 13:
FIG. 13 shows the results of a test (6 months) for organ transplantation onto rabbit knee joint cartilage defect, using a cell culture sponge having a cartilage matrix filling proportion at the transplant face of 33% and a film (degree of crosslinking of 6 or 13).
Figure 13:
Figure 13:
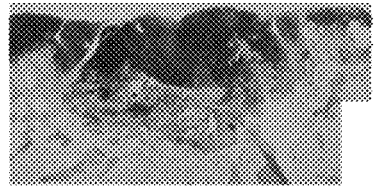
Figure 13:

The results are presented in FIG. 13. As shown in FIG. 13, in a case in which a sponge with cartilage matrix (cartilage matrix filling proportion: 33%) and a film having a degree of crosslinking of 6 were transplanted, and in a case in which a sponge with cartilage matrix (cartilage matrix filling proportion: 33%) and a film having a degree of crosslinking of 13 were transplanted, they both exhibited satisfactory suppression of the infiltration of fibrous soft tissue (evaluation: A) and sufficiently satisfactory cartilage regeneration (evaluation: A or higher). Furthermore, in a case in which the film having a degree of crosslinking of 6 was used, more remarkably satisfactory cartilage regeneration (evaluation: AA) was observed compared to the case of using the film having a degree of crosslinking of 13, and unexpectedly, it became obvious that superior results were obtained in a case in which the film having a degree of crosslinking of 6 was used.

[18] Biodegradability of Film

The film having a degree of crosslinking of 13 produced in the above sections [9] and [10] was placed at the rabbit cartilage defect site produced in the above section [15], and after one month and after two months, the rabbits were autopsied. Osteochondral tissue slices of the periphery of the transplantation site were produced. The tissue was subjected to formalin fixation, followed by paraffin embedment, and tissue slices including the transplant were produced. Regarding the slice staining, HE staining (haematoxylin and eosin staining) was carried out.

Figure 14:
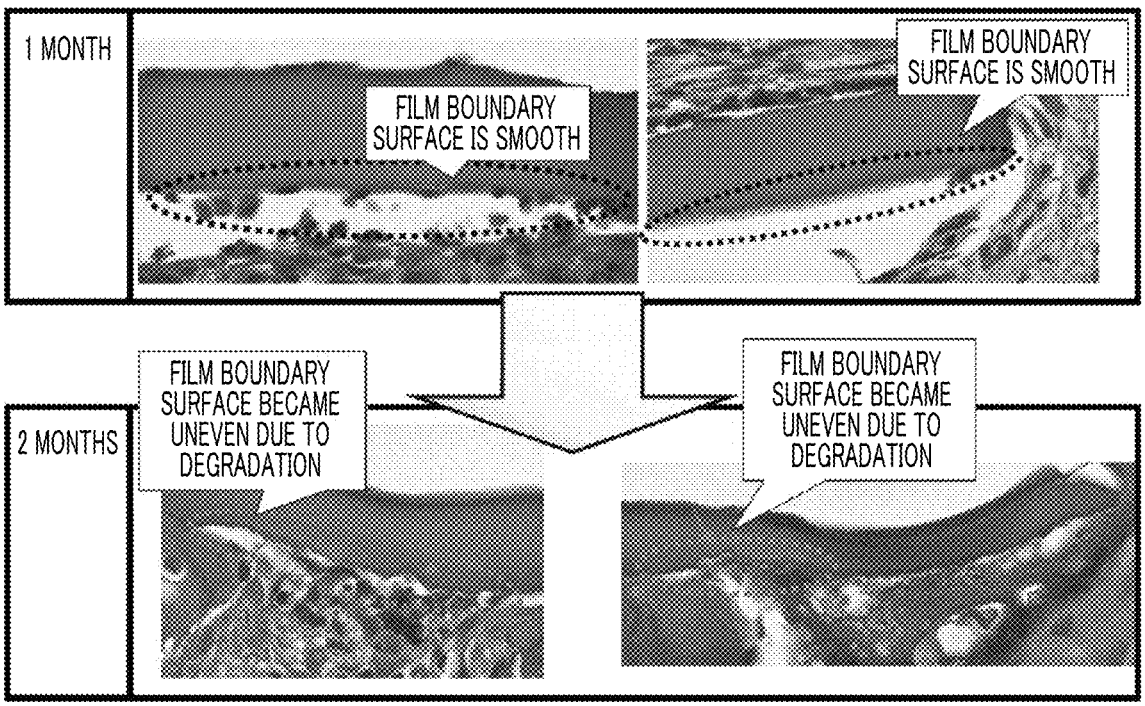
FIG. 14 shows in vivo decomposition of the film (degree of crosslinking 13).

The results are presented in FIG. 14. As shown in FIG. 14, it was clearly shown that even the film having a degree of crosslinking of 13, which had still been hardly decomposed one month after transplantation, definitely underwent decomposition after two months, from the corners of the film. From this, it was demonstrated that the films used had biodegradability.

[19] Evaluation of Effectiveness of Split Transplantation of Sponge with Cartilage Matrix (Sufficient Cartilage Matrix Filling Proportion)

In the actual clinical field, it is more desirable that transplantation therapy is enabled by using arthroscopy. In order to enable transplantation by arthroscopy, it is necessary that the transplant can pass through the arthroscopic portals. In order to do so, it is important that even in a case in which an osteochondral defect is filled with split transplants, cartilage regeneration is recognized to the same extent as in the case of using transplants that are not split. As a method for evaluating this, in a case in which a sponge with cartilage matrix having a sufficient cartilage matrix filling proportion was split once and then transplanted onto the site of defect, whether cartilage regeneration was recognized at the split portions was evaluated.

Figure 15:
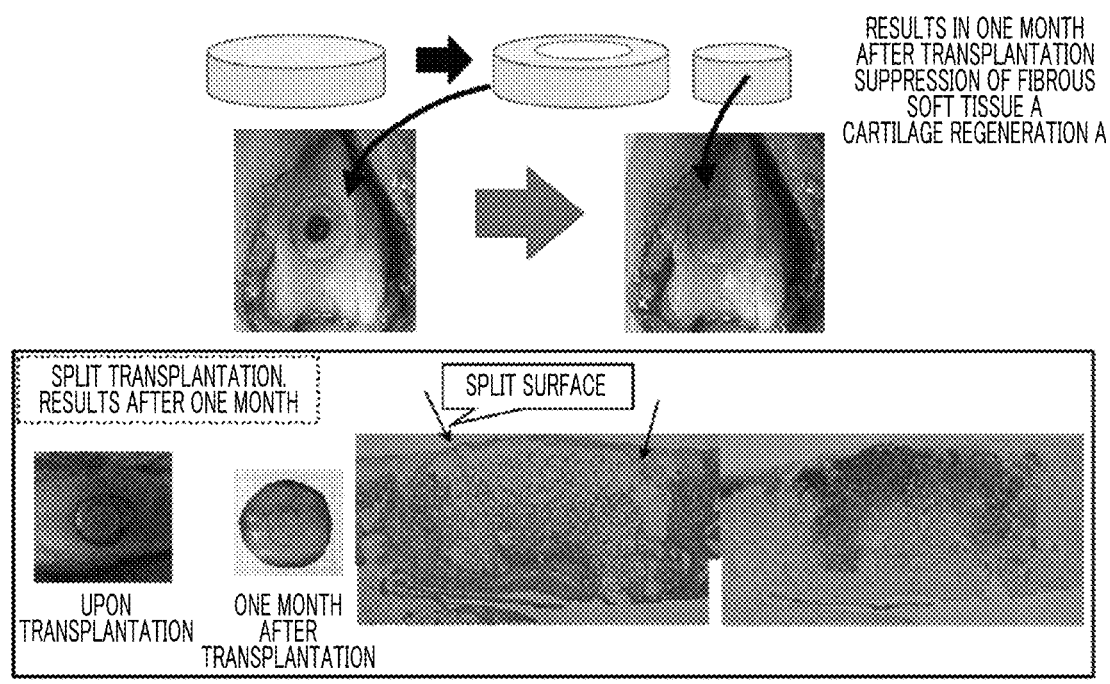
FIG. 15 shows the results of in vivo verification of split transplantation of a cartilage regenerative material.

The sponge with cartilage matrix (cartilage matrix filling proportion 90%) produced in the above sections [13] and [14] was split as shown in FIG. 15, and then the split sponges were transplanted together with the film having a degree of crosslinking of 13 produced in the above sections [9] and [10] onto the rabbit cartilage defect site produced in the above section [15]. Transplantation was carried out such that the film would exist on the transplant face (lower bone side). The rabbits were autopsied at the time point of one month after transplantation, and osteochondral tissue slices of the periphery of the site of transplantation were produced. The tissues were subjected to formalin fixation, followed by paraffin embedment, and tissue slices including the transplant were produced. Regarding the slice staining, HE staining (haematoxylin and eosin staining), or safranin O staining, or safranin O and fast green staining were carried out.

Here, regarding the film in the case of using a film, samples obtained by cutting the films prepared in the above section [9], which had a degree of crosslinking of 13 (measured in section [10]), respectively into the size of the low bottom face area (diameter: 5 mm) of the defect, were used.

The results are presented in FIG. 15. As shown in FIG. 15, satisfactory cartilage regeneration was recognized even at the split sites. From these results, it was found that even in a case in which a transplant has been split and transplanted, sufficient cartilage regeneration (evaluation: A) and sufficient suppression of the infiltration of fibrous soft tissue (evaluation: A) are manifested by having a sufficient cartilage matrix filling proportion and a film. Thereby, it was confirmed that even if transplantation is carried out after splitting the transplant once in order to allow the transplant to pass through the arthroscopic portals, there is no influence on the effectiveness.

[20] Verification of Whether Fixation to Site of Defect is Appropriate

In the actual clinical field, it is frequently desired that a transplant is fixed to the site of defect with pins after transplantation. It is necessary that whether this fixation is possible does not have a serious negative influence on cartilage regeneration even in a case in which the transplant is perforated with pins. As a method for evaluating this, verification of placing a sponge with cartilage matrix, which has a sufficient cartilage matrix filling proportion, onto an osteochondral defect site and then opening a through-hole by means of fixing pins, was performed. It is verified that even in a case where a through-hole that penetrates through the sponge with cartilage matrix, the film, and the bone at the defect bottom portion, is opened, there is no adverse effect on cartilage regeneration.

The sponge with cartilage matrix produced in the above sections [13] and [14] (cartilage matrix filling proportion 90%) and the film having a degree of crosslinking of 13 produced in the above sections [9] and [10] were transplanted onto the rabbit cartilage defect site produced in the above section [15], and subsequently, a through-hole that reached the sponge, the film and the lower bone was opened using a Kirschner wire having a diameter of 0.8 mm or a diameter of 1.5 mm. The rabbits were autopsied at the time point of passing one month in the state of having the through-hole maintained, and osteochondral tissue slices of the periphery of the site of transplantation were produced. The tissues were subjected to formalin fixation, followed by paraffin embedment, and thus tissue slices including the transplant were produced. Regarding the slice staining, HE staining (haematoxylin and eosin staining), or safranin O staining, or safranin O and fast green staining were carried out.

Here, regarding the film in the case of using a film, samples obtained by cutting the film having a degree of crosslinking of 13 (measured in section [10]), which was prepared in the above section [9], into the size of the low bottom face area (diameter: 5 mm) of the defect, were used. The samples were installed in the form in which the film existed on the transplant face (lower bone side).

Figure 16:
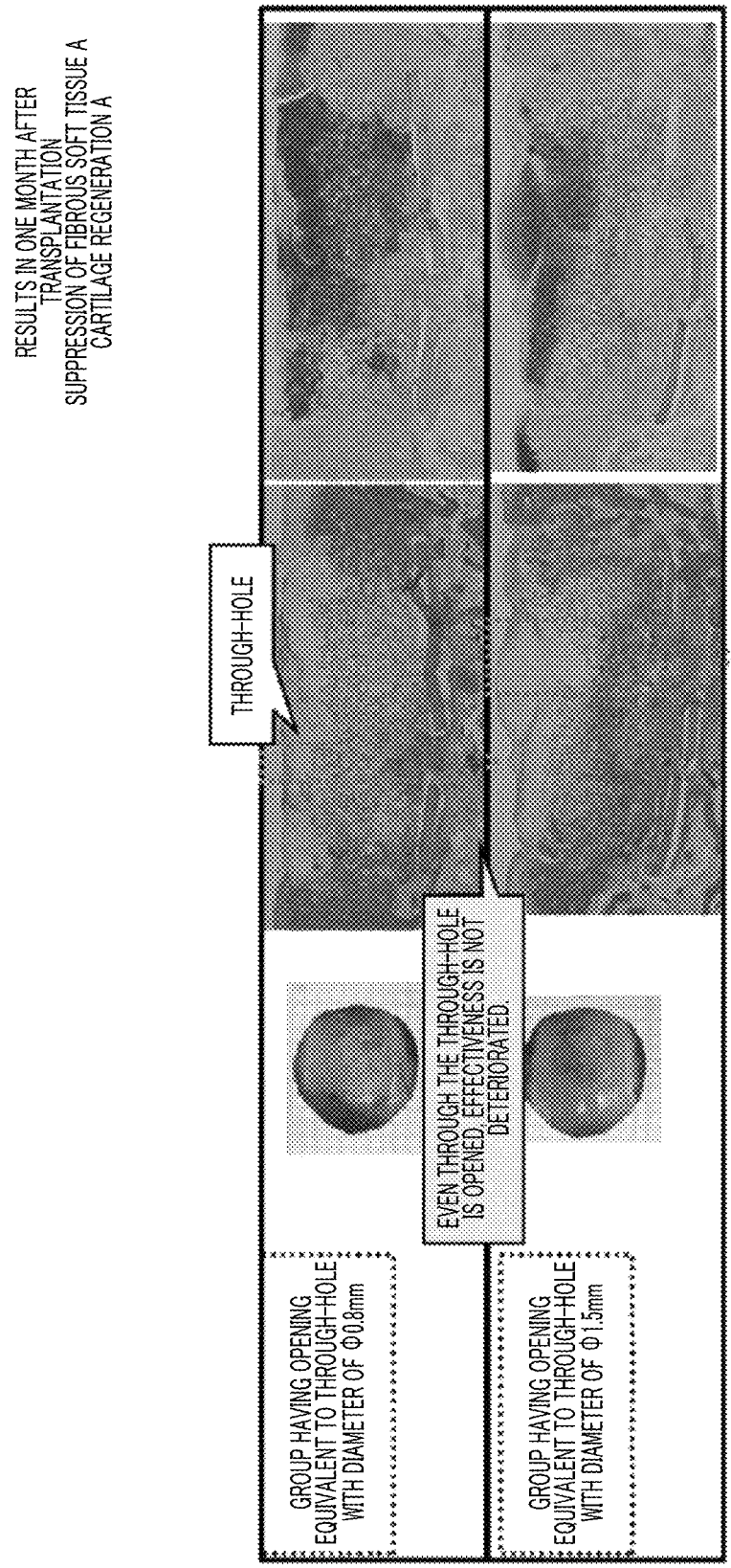
FIG. 16 shows the results of verification of the fixation of a cartilage regenerative material to a site of defect.

The results are presented in FIG. 16. As shown in FIG. 16, even in a case in which a through-hole having a diameter of 0.8 mm or a diameter of 1.5 mm was opened, there was no influence on the cartilage regeneration after one month (evaluation: A) and suppression of the infiltration of fibrous soft tissue (evaluation: A), and it became clear that satisfactory regeneration effect is shown. Thereby, it was found that it is possible to fix a transplant by piercing the transplant with fixing pins.

[21] Production of Pins Using Recombinant Peptide

Regarding a fixing pin that accomplishes fixation such as in the above section [19], it is required that such a pin has a performance that does not come out after piercing through a through-hole produced in the bone. At the same time, it is also desirable that the pin is bioabsorbable. Among existing products, for example, GRANDFIX (manufactured by Gunze, Ltd.) that is produced from poly-L-lactic acid, can be used.

Figure 17:
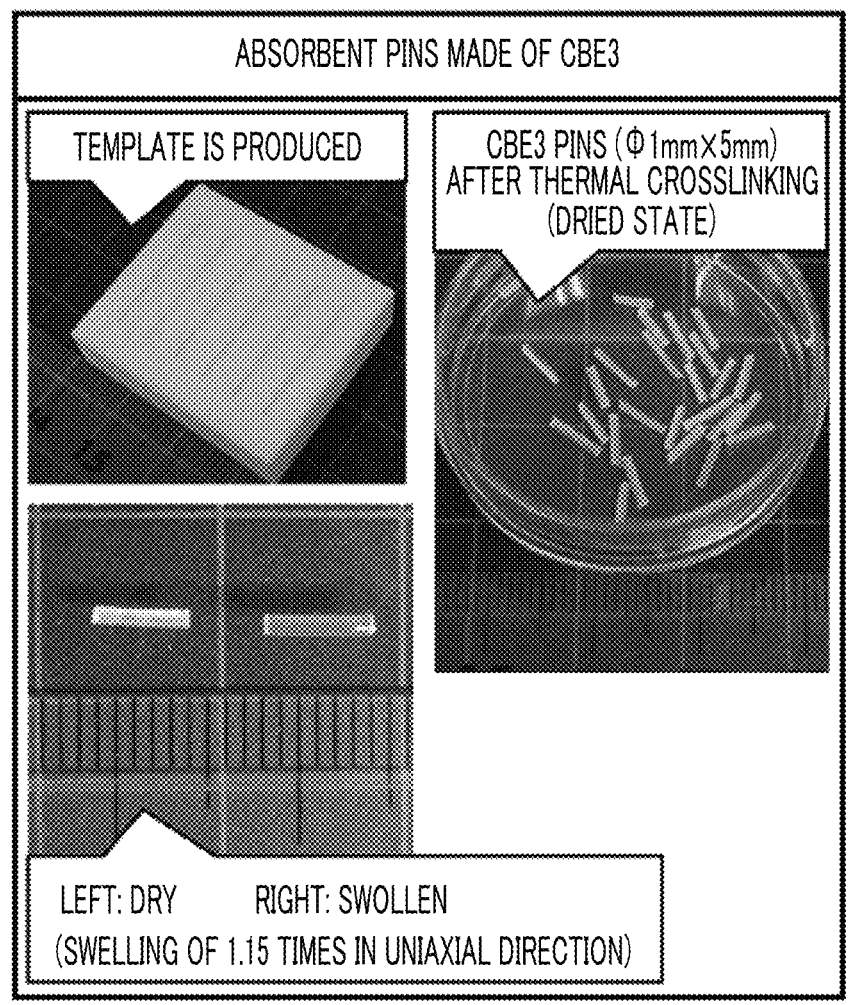
FIG. 17 shows the production of pins made of CBE3.

Furthermore, a pin made of a recombinant peptide could be produced using CBE3 of the above section [1]. A 10 mass % aqueous solution of CBE3 was prepared using the CBE3 of section [1]. Subsequently, the aqueous solution was caused to flow into a template made of TEFLON (registered trademark) shown in FIG. 17 and FIG. 18, and the aqueous solution was dried. Subsequently, CBE3 was subjected to thermal crosslinking by a heat treatment for 20 hours at 160° C. under reduced pressure, and thus pins (diameter: 1 mm, length: 5 mm) made of CBE3 were produced.

Figure 18:
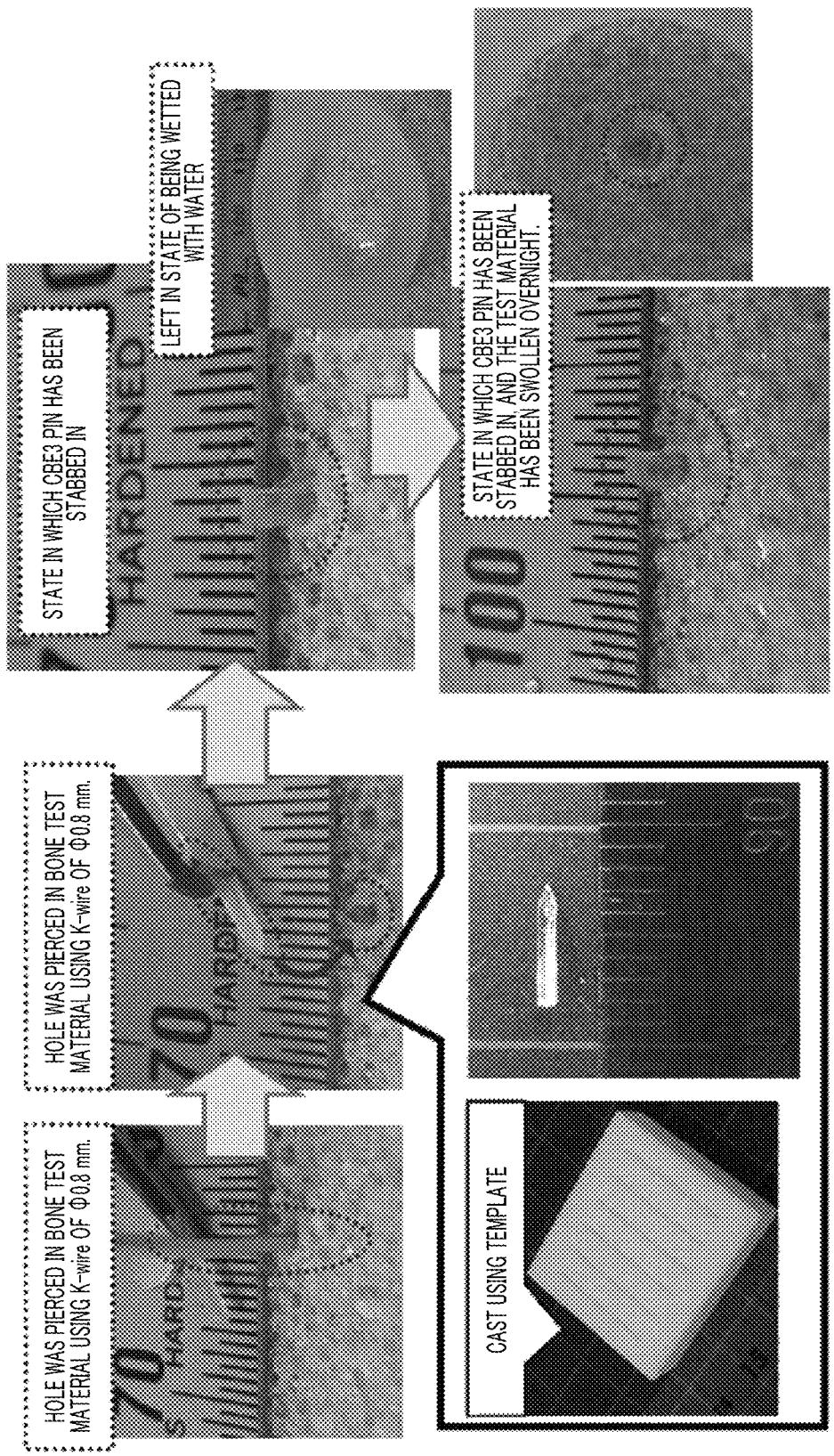
FIG. 18 shows the results of verification of fixability of a cartilage regenerative material by a pin made of CBE3.

On the other hand, a sponge bone test material was prepared as a substituent for bone, and a through-hole was produced using a Kirschner wire (K-wire) having a diameter of 0.8 mm was produced therein. The above-mentioned CBE3 pin was pierced into the hole having a diameter of 0.8 mm produced in the sponge bone test material, and the material was sufficiently swollen with water. This CBE3 pin maintained the shape without escaping even after being placed therein for one day. Thus, it was confirmed that the pin was a pin that can be used for fixation (FIG. 18).

SEQUENCE LIST

International Application Application 15F02955 Cartilage Regenerative Material and Method for Producing Same JP16058541 20160317—00200338451600554136 Normal 20160317153921201602251518509130_P1AP101_15_1. app Based on International Reception Patent Cooperation Treaty

What is claimed is:

1. A cartilage regenerative material comprising:
a porous body of a biocompatible polymer; and
a biocompatible polymer film,
wherein the porous body contains chondrocytes and cartilage matrix, and the cartilage matrix exists in a region of 10% or more of a region extending from a surface of a transplant face of the porous body to a depth of 150 μm along a thickness, and
wherein the biocompatible polymer film is a barrier isolating a portion or the entirety of the transplant face of the porous body from the site of transplantation.

2. The cartilage regenerative material according to claim 1,
wherein the cartilage matrix exists in a region of 20% or more of a region extending from the surface of the transplant face of the porous body to a depth of 150 μm along the thickness.

3. The cartilage regenerative material according to claim 1,
wherein the biocompatible polymer of the porous body is a recombinant peptide or a chemically synthesized peptide.

4. The cartilage regenerative material according to claim 1,
wherein the biocompatible polymer of the porous body is a recombinant gelatin or a chemically synthesized gelatin.

5. The cartilage regenerative material according to claim 4,
wherein the recombinant gelatin or the chemically synthesized gelatin is represented by Formula 1, $$A\text{-}[(Gly\text{-}X\text{-}Y)_n]_m\text{-}B \qquad \text{Formula 1:}$$

in Formula 1, n units of X each independently represent any amino acid residue; n units of Y each independently represent any amino acid residue; m represents an integer from 2 to 10; n represents an integer from 3 to 100; A represents an arbitrary amino acid residue or amino acid sequence; and B represents an arbitrary amino acid residue or amino acid sequence.

6. The cartilage regenerative material according to claim 4,
wherein the recombinant gelatin or the chemically synthesized gelatin is any one of the following:
a peptide comprising the amino acid sequence set forth in SEQ ID NO:1;
a peptide having biocompatibility and comprising an amino acid sequence obtained by modifying the amino acid sequence set forth in SEQ ID NO:1 by deletion, substitution or addition of one or several amino acid residues; and
a peptide having biocompatibility and comprising an amino acid sequence having at least 80% sequence identity with the amino acid sequence set forth in SEQ ID NO:1.

7. The cartilage regenerative material according to claim 1,
wherein the porous body is obtainable by freeze-drying an aqueous solution containing a biocompatible polymer.

8. The cartilage regenerative material according to claim 1,
wherein the biocompatible polymer of the biocompatible polymer film is a recombinant gelatin or a chemically synthesized gelatin.

9. The cartilage regenerative material according to claim 8,
wherein the biocompatible polymer of the biocompatible polymer film is represented by Formula 1, $$A\text{-}[(Gly\text{-}X\text{-}Y)_n]_m\text{-}B \qquad \text{Formula 1:}$$

in Formula 1, n units of X each independently represent any amino acid residue; n units of Y each independently represent any amino acid residue; m represents an integer from 2 to 10; n represents an integer from 3 to 100; A represents an arbitrary amino acid residue or amino acid sequence; and B represents an arbitrary amino acid residue or amino acid sequence.

10. The cartilage regenerative material according to claim 8,
wherein the biocompatible polymer of the biocompatible polymer film is any one of the following:
a peptide comprising the amino acid sequence set forth in SEQ ID NO:1;
a peptide having biocompatibility and comprising an amino acid sequence obtained by modifying the amino acid sequence set forth in SEQ ID NO:1 by deletion, substitution or addition of one or several amino acid residues; and
a peptide having biocompatibility and comprising an amino acid sequence having at least 80% sequence identity with the amino acid sequence set forth in SEQ ID NO:1.

11. The cartilage regenerative material according to claim 1,
wherein the biocompatible polymer of the biocompatible polymer film has a degree of crosslinking of 4 to 8.

12. The cartilage regenerative material according to claim 1,
wherein the rate of decomposition, which is represented by Formula 4, of the biocompatible polymer of the biocompatible polymer film is 0.1 to 20 mass %/hour, $$\text{Rate of decomposition} = ((W-We)-wo)/wo/T \qquad \text{Formula 4:}$$

in Formula 4, W represents the mass of a tube containing a sample, which is recorded after decomposition by a collagenase and freeze-drying; We represents the blank mass of the tube that has been recorded in advance; wo represents the actual amount of addition of the sample; and T represents the time taken for shaking in a collagenase solution.

13. The cartilage regenerative material according to claim 1, wherein the rate of decomposition, which is represented by Formula 4, of the biocompatible polymer of the biocompatible polymer film is 5 to 10 mass %/hour, $$\text{Rate of decomposition} = ((W-We)-wo)/wo/T \quad \text{Formula 4:}$$

in Formula 4, W represents the mass of a tube containing a sample, which is recorded after decomposition by a collagenase and freeze-drying; We represents the blank mass of the tube that has been recorded in advance; wo represents the actual amount of addition of the sample; and T represents the time taken for shaking in a collagenase solution.

14. The cartilage regenerative material according to claim 1, wherein the chondrocytes are at least one type of chondrocytes selected from the group consisting of articular cartilage-derived chondrocytes, auricular cartilage-derived chondrocytes, nasal cartilage-derived chondrocytes, iPS cell-derived chondrocytes, ES cell-derived chondrocytes, mesenchymal stem cell-derived chondrocytes, and chondrocytes obtained by a direct reprogramming method.

15. The cartilage regenerative material according to claim 1, wherein the cartilage matrix exists in a region occupying 10% or more of a region extending from the surface of an articular cavity face of the porous body to a depth of 150 μm along the thickness.

16. The cartilage regenerative material according to claim 1, further comprising:
a pin of a biocompatible polymer.

17. A method for regenerating cartilage, the method comprising transplanting the cartilage regenerative material of claim 1 to a patient in need of cartilage regeneration.

* * * * *